(12) United States Patent
Pastor et al.

(10) Patent No.: US 6,774,238 B2
(45) Date of Patent: Aug. 10, 2004

(54) SUBSTITUTED 5-ARYL-2-(2-HYDROXYPHENYL)-2H-BENZOTRIAZOLE UV ABSORBERS, COMPOSITIONS STABILIZED THEREWITH AND PROCESS FOR PREPARATION THEREOF

(75) Inventors: Stephen D. Pastor, Danbury, CT (US); Andrew B. Naughton, Mobile, AL (US); Robert Detlefsen, Putnam Valley, NY (US); Mervin G. Wood, Poughquag, NY (US); Joseph Suhadolnik, Yorktown Heights, NY (US); Anthony DeBellis, Stony Point, NY (US); Deborah DeHessa, Poughkeepsie, NY (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/602,094

(22) Filed: Apr. 17, 2003

(65) Prior Publication Data

US 2004/0092628 A1 May 13, 2004

Related U.S. Application Data

(62) Division of application No. 09/722,876, filed on Nov. 27, 2000, now Pat. No. 6,649,770.

(51) Int. Cl.[7] ............................................. C07D 249/20
(52) U.S. Cl. ....................................................... 548/260
(58) Field of Search ........................................ 548/260

(56) References Cited

U.S. PATENT DOCUMENTS

| | | | | |
|---|---|---|---|---|
| 4,226,763 A | * | 10/1980 | Dexter et al. .............. | 260/45.8 |
| 4,275,004 A | * | 6/1981 | Winter et al. ............... | 260/206 |
| 4,278,589 A | * | 7/1981 | Dexter et al. .............. | 260/45.8 |
| 4,315,848 A | * | 2/1982 | Dexter et al. .............. | 260/45.8 |
| 4,347,180 A | * | 8/1982 | Winter et al. .............. | 260/206 |
| 4,396,712 A |   | 8/1983 | Kinoshita et al. .......... | 430/614 |
| 4,999,433 A |   | 3/1991 | Prestel et al. .............. | 548/260 |
| 5,229,521 A |   | 7/1993 | Luisoli et al. .............. | 548/260 |
| 5,278,314 A | * | 1/1994 | Winter et al. .............. | 548/259 |
| 5,280,124 A | * | 1/1994 | Winter et al. .............. | 548/259 |
| 5,332,655 A |   | 7/1994 | Shono et al. ............... | 430/512 |
| 5,436,349 A |   | 7/1995 | Winter et al. .............. | 548/259 |
| 5,516,914 A |   | 5/1996 | Winter et al. .............. | 548/259 |
| 5,554,760 A | * | 9/1996 | Winter et al. .............. | 548/260 |
| 5,563,242 A | * | 10/1996 | Winter et al. ............... | 524/91 |
| 5,574,166 A | * | 11/1996 | Winter et al. .............. | 548/260 |
| 5,607,987 A | * | 3/1997 | Winter et al. ............... | 524/91 |
| 5,977,219 A |   | 11/1999 | Ravichandran et al. ....... | 524/91 |

FOREIGN PATENT DOCUMENTS

| | | | |
|---|---|---|---|
| EP | 363820 | * | 10/1989 |
| GB | 980886 | * | 1/1965 |
| GB | 2319035 | * | 5/1998 |
| JP | 593164 | * | 4/1993 |
| WO | 00/22037 | * | 4/2000 |

OTHER PUBLICATIONS

J. L. Gerlock et al., Proc. 36th Annual Tech. Sym., May 18, 1993.*
A. Suzuki, Pure & Applied Chem., vol. 66, No. 2, pp. 213–222 (1994).*
B. E. Huff et al., Organic Synthesis, vol. 75, pp. 53–60 (1998).*
J. P. Wolfe et al., J. Am. Chem. Soc., (1999), vol. 121, pp. 9550–9561.
Derwent Abstr. 1996–299547 for JP 11500579.
Chemical Abstract 131:199658x for Z. Wang et al., Huadong Ligong Daxue Xuebao, vol. 25, No. 2, (1999) pp. 167–169.

* cited by examiner

Primary Examiner—Patricia L. Morris
(74) Attorney, Agent, or Firm—Tyler A. Stevenson

(57) ABSTRACT

Compounds of formula I or II

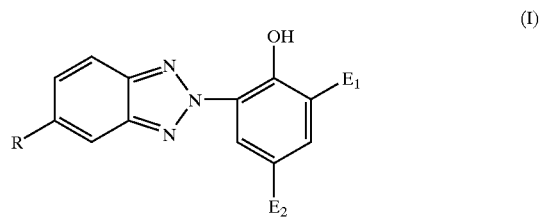

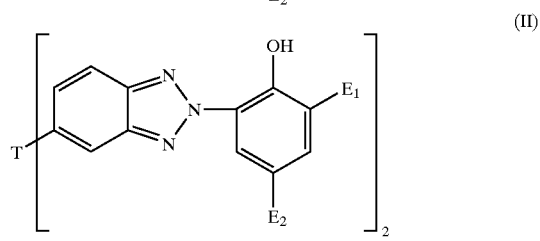

where R is an aryl moiety, such as phenyl, naphthyl or biphenylyl, or is phenyl substituted by one or more trifluoromethyl, bromo or cyano, and $E_1$ and $E_2$ are independently hydrogen, alkyl, aralkyl and the like are prepared by reaction of a benzotriazole substituted on the 5-position of the benzo ring by a halogen atom with a arylboronic acid or ester in the presence of a transition-metal catalyst, such as palladium(II) diacetate. The benzotriazole compounds of formula I are particularly efficacious as stabilizers for automotive coatings and candle wax.

9 Claims, No Drawings

SUBSTITUTED 5-ARYL-2-(2-HYDROXYPHENYL)-2H-BENZOTRIAZOLE UV ABSORBERS, COMPOSITIONS STABILIZED THEREWITH AND PROCESS FOR PREPARATION THEREOF

This is a divisional of application Ser. No. 09/722,876, filed Nov. 27, 2000, now U.S. Pat. No. 6,649,770.

BACKGROUND OF THE INVENTION

The instant invention pertains to novel 5-aryl substituted benzotriazole UV absorbers, to a novel process for their preparation and to compositions stabilized by said benzotriazoles.

The benzotriazoles have long been an important class of UV absorbers and have gained wide commercial importance and acceptance for many industrial applications. The prior art is replete with references to their manufacture and utility. However, as requirements become ever more stringent and demanding, the search for still more stable and durable benzotriazoles continues. The gradual phase out of HAPS solvents, such as xylene, because of environmental concerns and their replacement with non-HAPS solvents, such as esters, ethers or ketones, and increased durability requirements for automotive coatings make this search more urgent. Indeed, the automotive industry is most concerned about UVA losses from automotive paints and coatings as seen in the publication by J. L. Gerlock et al., Proc. 36th Annual Tech. Sym. (Cleveland Coating Society), May 18, 1993.

U.S. Pat. Nos. 4,226,763; 4,278,589; 4,315,848; 4,275,004; 4,347,180; 5,554,760; 5,563,242; 5,574,166 and 5,607,987 describe selected benzotriazoles, substituted in the 3-position of the hydroxyphenyl ring by an α-cumyl group, which show very good durability in automotive coatings. These benzotriazoles represent the present state of the art. The instant invention is directed at preparing benzotriazoles which exhibit still better durability and low loss rates from the prior art benzotriazoles.

U.S. Pat. Nos. 5,278,314; 5,280,124; 5,436,349 and 5,516,914 describe red-shifted benzotriazoles. These benzotriazoles are substituted in the 3-position of the phenyl ring with an α-cumyl group and at the 5-position of the benzo ring by thio ethers, alkylsulfonyl or phenylsulfonyl moieties. Red-shifting the benzotriazoles is desirable for spectral reasons. A group at the 5-position which is also electron withdrawing provides additional benefits in low loss rates and durability as found in the instant invention. Missing from these patents are any alkylsulfones with seven or fewer carbon atoms. When such sulfonyl substituents are combined with specifically α-cumyl moieties, extremely durable compounds result which, due to the bulk of the α-cumyl moiety have sufficiently low volatility to be useful in coating and other polymer systems.

The presence of an α-cumyl or phenyl group ortho to the hydroxy group on the phenyl ring exerts a surprisingly large positive effect on benzotriazole photostability in coatings and photographic gel systems. The magnitude of this effect, particularly when compared to a tert-butyl group in that position, is well beyond prediction. The combination of both an electron withdrawing group on the benzo ring and an α-cumyl or phenyl group on the phenyl ring in the same molecule leads to extremely desirable properties in coating systems when high UV absorber permanence is critical.

Novel compounds meeting these parameters as being extremely stable in aggressive use environments constitute a first portion of this invention.

The presence of the electron withdrawing moiety at the 5-position of the benzo ring has a powerful stabilizing effect on benzotriazoles in general and is observed in other polymer systems such as polycarbonate and poly(vinyl chloride) substrates as well. However, the effect of having an α-cumyl or phenyl group ortho to the hydroxy moiety on the phenyl ring is much smaller to non-existent in some polymer systems such as polycarbonate or poly(vinyl chloride) even though critical for coating systems as described above.

In addition to being more photostable, the compounds of this invention are red-shifted, absorbing strongly in the 350–400 nm wavelength range. While such red-shifting is desirable in that a greater portion of the UV spectrum is absorbed, this can also introduce color if the absorption beyond 400 nm is significant. This can limit the use of such compounds, particularly in systems such as polycarbonate glazing applications or present difficulties in various pigmented systems.

It is found that the nature of the substituent ortho to the hydroxyl group on the phenyl ring has an unexpected impact on color imparted to the substrate by the benzotriazole. Thus, relatively subtle differences in substitution on the phenyl ring can have a large impact on the resulting color and the applicability of the benzotriazole in specific color sensitive applications. There are striking differences between having hydrogen, alkyl or α-cumyl at this 3-position.

Furthermore, U.S. Pat. No. 5,977,219 teaches that, when the 5-position of the benzo ring is substituted with a trifluoromethyl group, the resulting benzotriazole not only exhibits the same or greater enhanced stability when incorporated into thermoplastic resins, but also imparts less color than related benzotriazoles substituted at the 5-position with other electron withdrawing moieties such as sulfonyl or carbonyl. These trifluoromethyl compounds also absorb strongly in the 350–400 nm wavelength range despite the low color and are extremely compatible in a wide range of substrates such as acrylic resins, hydrocarbons, polycarbonates and poly(vinyl chloride).

There are a multitude of general references to benzotriazoles having in the 5-position of the benzo ring electron withdrawing groups such as esters, amides, sulfones and the like that are not substituted in the 3-position of the phenyl ring by an α-cumyl or phenyl moiety. In many of these references the broadly described compounds are unexemplified and no teaching or appreciation taught of the positive effect on photostability described in this invention. In any event, the vast majority of these structures fall well outside the scope of instant invention.

Japanese 1996-299547 discloses the use of heterocyclic compounds as non-aqueous electrolytes for lithium batteries. These heterocyclic compounds included benzotriazoles substituted on the benzo ring by hydrogen, methyl, ethyl, amino, hydroxyl, 2-pyridyl or phenyl; and substituted on the hydroxyphenyl ring by at the 5-position by a methyl group and at the 3-position by hydrogen, methyl, ethyl, amino, hydroxyl, 2-pyridyl or phenyl.

U.S. Pat. No. 4,396,712 describes generically benzotriazole compounds which are substituted at the 5-position of the benzo ring by phenyl as light stabilizers for photothermographic film. The only compound disclosed specifically is 5-phenyl-2-(2-hydroxy-3,5-di-tert-amylphenyl)-2H-benzotriazole. The benzotriazole UV absorbers provide improved storage stability by stabilizing the silver salts (oxidizing agents) in these dry image forming materials. Only selected low molecular weight benzotriazoles are suitable since the benzotriazole must be compatible with other components of the image forming materials.

A. Suzuki, Pure & Applied Chem., 66, No. 2, 213 (1994) describes a new synthetic method involving the reaction of sterically hindered aryl boronic acids or esters with sterically hindered haloarenes in the presence of palladium(II) catalysts. This reaction has become known as the Suzuki reaction.

B. E. Huff et al., Organic Synthesis, 75, 53 (1998) describe the synthesis of unsymmetrical biaryls using a modified Suzuki cross-coupling to form 4-biphenylcarboxaldehyde.

J. P. Wolfe, et al., J. Am. Chem. Soc., 1999, 121, 9550 describe the use of highly active palladium catalysts for Suzuki coupling reactions.

WO 00/22037 describes the stabilization of solid, shaped and colored wax articles using a malonate UV absorber which may be substituted by a hindered amine group.

Japanese Hei 5-93164 discloses the use of benzotriazole UV absorbers and hindered amines in stabilizing pigmented wax crayons.

Copending U.S. patent applications Ser. Nos. 09/496,084; 09/495,495 and 09/495,496 all describe the stabilization of candle wax using other types of benzotriazole UV absorbers.

DETAILED DESCRIPTION

The instant invention pertains to compounds of formula I or II

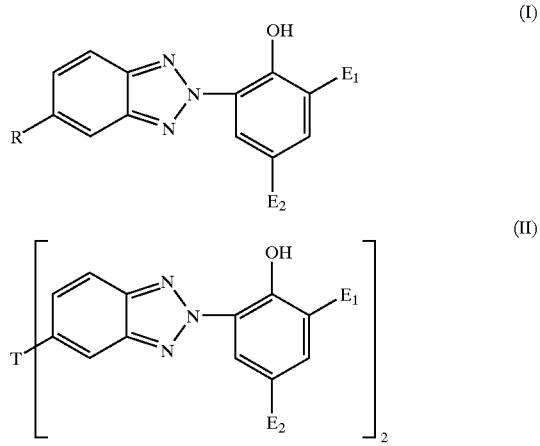

wherein
R is phenyl, naphthyl, biphenylyl, 9-phenanthryl or said phenyl, naphthyl, biphenylyl or 9-phenanthryl substituted by one to three alkyl of 1 to 18 carbon atoms, phenylalkyl of 7 to 15 carbon atoms, $R_3S$—, $R_3SO$—, $R_3SO_2$, aryl of 6 to 10 carbon atoms, perfluoroalkyl of 1 to 12 carbon atoms, halogen, nitro, cyano, carboxyl, alkoxycarbonyl of 2 to 19 carbon atoms, hydroxyl, alkoxy of 1 to 18 carbon atoms, aryloxy of 6 to 10 carbon atoms, aralkoxy of 7 to 15 carbon atoms, vinyl, acetyl, acetamido, amino, dialkylamino of 2 to 12 carbon atoms, formyl, thioalkoxy of 1 to 18 carbon atoms, hydroxymethyl, amino-methyl, halomethyl, sulfato, phosphato or where any two substituents form a benzo ring with the aryl moiety to which they are attached,
T is a direct bond, 1,4-phenylene or said phenylene substituted by one or two alkyl of 1 to 12 carbon atoms,
$R_3$ is alkyl of 1 to 18 carbon atoms, phenylalkyl of 7 to 15 carbon atoms or aryl of 6 to 10 carbon atoms,
$E_1$ is hydrogen, straight or branched alkyl of 1 to 24 carbon atoms, phenylalkyl of 7 to 15 carbon atoms, phenyl, or said phenyl or said phenylalkyl substituted on the phenyl ring by 1 to 4 alkyl of 1 to 4 carbon atoms,
$E_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; or $E_2$ is alkyl of 1 to 24 carbon atoms or alkenyl of 2 to 18 carbon atoms substituted by one or more —OH, —$OCOE_3$, —$NH_2$, —$NHCOE_3$ or —$COOE_3$, or mixtures thereof; or said alkyl or said alkenyl interrupted by one or more —O— which can be unsubstituted or substituted by one or more —OH groups; where $E_3$ is hydrogen or alkyl of 1 to 24 carbon atoms, and where said alkyl is interrupted by one or more —O— and which can be substituted by one or more —OH or —$OR_{21}$ groups where $R_{21}$ is alkyl of 1 to 12 carbon atoms; and
with the proviso that 5-phenyl-2-(2-hydroxy-3,5-di-tert-amylphenyl)-2H-benzotriazole is excluded; and
with the further proviso that, when $E_1$ is hydrogen, methyl or ethyl and $E_2$ is methyl or ethyl, R is not phenyl.

Another embodiment are the compounds of formula I are those where R is phenyl, 2-naphthyl, 3-biphenylyl, 4-biphenylyl, 9-phenanthryl, 2-trifluoromethylphenyl, 3-trifluoromethylphenyl, 4-trifluoromethylphenyl, 3,5-ditrifluoromethylphenyl, 4-cyanophenyl, 3-methylphenyl, 3-isopropylphenyl, 3-fluorophenyl, 3-chlorophenyl, 3-bromophenyl, 3-iodophenyl, 3-methoxyphenyl, 3-ethoxyphenyl, 3-benzyloxyphenyl, 3-hydroxyphenyl, 3-hydroxymethylphenyl, 3-thiomethylphenyl, 3-bromomethylphenyl, 3-cyanophenyl, 3-vinylphenyl, 3-acetylphenyl, 3-aminophenyl, 3-acetamidophenyl, 3-formylphenyl, 3-isothiocyanophenyl, 2-ethylphenyl, 2-cyanophenyl, 2-acetylphenyl, 2-bromomethylphenyl, 2-bromophenyl, 2-vinylphenyl, 2-aminophenyl, 2-hydroxyphenyl, 2-ethoxyphenyl, 2-fluorophenyl, 2-chlorophenyl, 2-methoxyphenyl, 2-formylphenyl, 2-methylphenyl, 4-n-butylphenyl, 4-n-nonylphenyl, 4-methoxycarbonylphenyl, 4-cyanomethylphenyl, 4-aminomethylphenyl, 4-isobutylphenyl, 4-iodophenyl, 4-thioethylphenyl, 4-bromomethylphenyl, 4-benzyloxyphenyl, 4-acetylphenyl, 4-dimethylaminophenyl, 4-hydroxyphenyl, 4-isopropylphenyl, 4-tert-butylphenyl, 4-aminophenyl, 4-n-amylphenyl, 4-ethylphenyl, 4-hydroxymethylphenyl, 4-ethoxyphenyl, 4-vinylphenyl, 4-formylphenyl, 4-carboxyphenyl, 4-thiomethylphenyl, 4-phenoxyphenyl, 4-methoxyphenyl, 4-methylphenyl, 4-chlorophenyl, 4-fluorophenyl, 4-bromophenyl, 2,6-dimethylphenyl, 3,5-dichlorophenyl, 3,5-dimethylphenyl, 3,5-dibromophenyl, 3,5-difluorophenyl, 3-chloro-4-fluorophenyl, 3,4-difluorophenyl, 3-amino-4-methylphenyl, 3,4-dichlorophenyl, 3-hydroxy-4-methylphenyl, 3-amino-4-methylphenyl, 3-fluoro-4-bromophenyl or 3-fluoro-4-formylphenyl, and where $E_1$ and $E_2$ are independently straight or branched chain alkyl of 4 to 24 carbon atoms or phenylalkyl of 7 to 15 carbon atoms, or $E_1$ is additionally phenyl.

Another embodiment of the instant invention are compounds of formula II where T is a direct bond, 1,4-phenylene or 2,5-di-n-hexyl-1,4-phenyene and where $E_1$ and $E_2$ are independently a straight or branched chain alkyl of 4 to 24 carbon atoms or phenylalkyl of 7 to 15 carbon atoms.

Another embodiment of the instant invention are the compounds of formula I or II where R is phenyl, 2-trifluoromethylphenyl, 3-trifluoromethylphenyl, 4-trifluoromethylphenyl, 3,5-di-trifluoromethylphenyl, 4-cyanophenyl, 4-methoxyphenyl or 1,1'-biphenyl-4-ylphenyl, T is 1,4-phenylene, $E_1$ is phenyl or α-cumyl, and $E_2$ is tert-butyl or tert-octyl.

Still another embodiment of the instant invention are compounds of formula I where R is phenyl or 4-trifluoromethylphenyl; $E_1$ is α-cumyl; and $E_2$ is tert-octyl.

The instant invention also pertains to the method of making the instant compounds of formula I or II

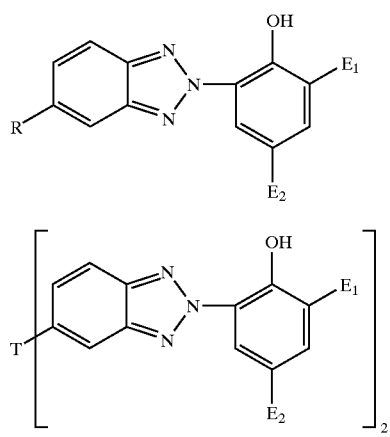

where R, T, $E_1$ and $E_2$ are as defined above,
by the reaction of an arylboronic acid or ester of formula III or IV

where $R_1$ and $R_2$ are independently hydrogen, alkyl of 1 to 12 carbon atoms, or $R_1$ and $R_2$ together are alkylene of 2 to 4 carbon atoms;

with a 5-substituted benzotriazole of formula V

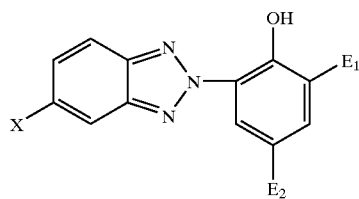

where X is chloro, bromo or iodo, or tosylate,
in the presence of an effective amount of a palladium(II) catalyst and optionally in the additional presence of a ligand, such as triphenylphosphine, at a temperature between 10 to 100° C., preferably between 50 to 95° C.

When a ligand is used, the ligand is triphenylphosphine, 2-(di-tert-butylphosphino)biphenyl, 1,1'-bis[2,4,8,10-tetrakis(tert-butyl)-dibenzo[d,f][1,3,2]dioxaphosphepin-6-yl]ferrocene, tris(2,4-di-tert-butylphenyl)phosphite or 2,2', 2"-nitrilo-[triethyl-tris(3,3',5,5'-tetra-tert-butyl-1,1'-biphenyl-2,2'-diyl)phosphite]. In another embodiment, the ligand is triphenylphosphine.

Preferably the amount of palladium(II) catalyst is 0.01 to 10 mol percent.

In one embodiment of the invention, an anhydrous process is used with dioxane as solvent and potassium fluoride as a base; or the process can be run using n-propanol or isopropanol as solvent with a small amount of water and aqueous sodium carbonate as a base.

When any of $R_1$ to $R_3$ or any of $E_1$ to $E_3$ is alkyl, such groups are, straight or branched chain, for example, methyl, ethyl, n-propyl, isopropyl, n-butyl, isobutyl, sec-butyl, tert-butyl, tert-amyl, n-hexyl, n-octyl, 2-ethylhexyl, tert-octyl, lauryl, undecyl, tert-dodecyl, tridecyl, n-hexadecyl, n-octadecyl and eicosyl; when any of said radicals is alkenyl, such groups are, for example, allyl, methallyl. 2-n-hexenyl, 4-n-octenyl or oleyl; when any of said radicals is cycloalkyl, such groups are, for example, cyclopentyl, cyclohexyl, cycloheptyl, cyclooctyl or cyclododecyl; when any of said radicals are phenylalkyl, such groups are, for example, benzyl, α-phenethyl, 2-phenethyl, α-methylbenzyl or α,α-dimethylbenzyl; and when any of said radicals is aryl, they are, for example, phenyl, α-naphthyl or β-naphthyl or when substituted by alkyl are, for example, tolyl and xylyl. When alkyl is substituted by one or more —O— groups and/or substituted by one or more —OH, these groups can be hydroxymethyl, 2-hydroxyethyl or 2-hydroxypropyl or can be, for example, —(OCH$_2$CH$_2$)$_w$OH or —(OCH$_2$CH$_2$)$_w$OR$_{21}$ where w is 1 to 12 and $R_{21}$ is alkyl of 1 to 12 carbon atoms; when any of said radicals is halogen, they are, for example, fluoro, chloro, bromo or iodo; when any of said radicals is alkoxycarbonyl, they are, for example, methoxycarbonyl, ethoxycarbonyl, butoxycarbonyl, hexyloxycarbonyl, octyloxycarbonyl, or dodecyloxycarbonyl; when any of said radicals is alkoxy or aryloxy, they are, for example, the same alkyl or same aryl definition as seen above.

The instant invention also pertains to a composition stabilized against thermal, oxidative or light-induced degradation which comprises,
(a) an organic material subject to thermal, oxidative or light-induced degradation, and
(b) an effective stabilizing amount of a compound of formula I or II

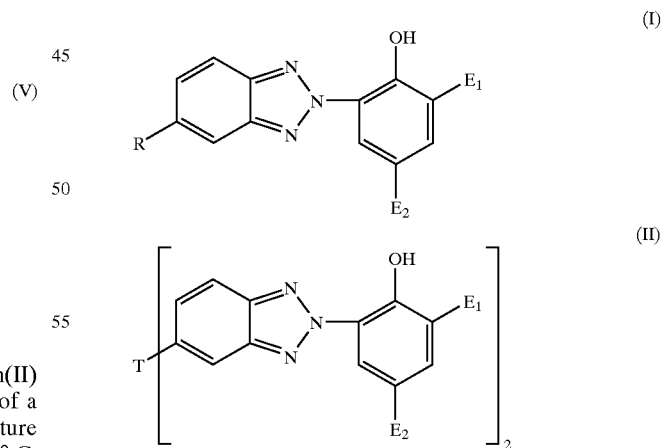

wherein
R is phenyl, naphthyl, biphenylyl, 9-phenanthryl or said phenyl, naphthyl, biphenylyl or 9-phenanthryl substituted by one to three alkyl of 1 to 18 carbon atoms, phenylalkyl of 7 to 15 carbon atoms, $R_3S$—, $R_3SO$—, $R_3SO_2$, aryl of 6 to 10 carbon atoms, perfluoroalkyl of 1 to 12 carbon atoms, halogen, nitro, cyano, carboxyl, alkoxycarbonyl of 2 to 19 carbon atoms, hydroxyl, alkoxy of 1 to 18 carbon atoms, aryloxy of 6 to 10 carbon atoms, aralkoxy of 7 to 15 carbon atoms, vinyl, acetyl, acetamido, amino, dialkylamino of 2 to 12 carbon atoms, formyl, thioalkoxy of 1 to 18 carbon atoms, hydroxymethyl, aminomethyl, halomethyl, sulfato, phosphato or where any two substituents form a benzo ring with the aryl moiety to which they are attached, T is a direct bond, 1,4-phenylene or said phenylene substituted by one or two alkyl of 1 to 12 carbon atoms, $R_3$ is alkyl of 1 to 18 carbon atoms, phenylalkyl of 7 to 15 carbon atoms or aryl of 6 to 10 carbon atoms, $E_1$ is hydrogen, straight or branched alkyl of 1 to 24 carbon atoms, phenylalkyl of 7 to 15 carbon atoms, phenyl, or said phenyl or said phenylalkyl substituted on the phenyl ring by 1 to 4 alkyl of 1 to 4 carbon atoms, $E_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; or $E_2$ is alkyl of 1 to 24 carbon atoms or alkenyl of 2 to 18 carbon atoms substituted by one or more —OH, —OCOE$_3$, —NH$_2$, —NHCOE$_3$ or —COOE$_3$, or mixtures thereof; or said alkyl or said alkenyl interrupted by one or more —O— which can be unsubstituted or substituted by one or more —OH groups; where $E_3$ is hydrogen or alkyl of 1 to 24 carbon atoms, and where said alkyl is interrupted by one or more —O— and which can be substituted by one or more —OH or —OR$_{21}$ groups where $R_{21}$ is alkyl of 1 to 12 carbon atoms.

The organic material is a natural, semi-synthetic or synthetic polymer, such as a thermoplastic polymer.

In other embodiments, the polymer is a polyolefin or polycarbonate, such as polyethylene or polypropylene; or polypropylene; or the polymer is a styrenic, ABS, a nylon, a polyester such as poly(ethylene terephthalate) or poly(butylene terephthalate), a polyurethane, an acrylate, a rubber modified styrenic, poly(vinyl chloride), poly(vinyl butyral), polyacetal (polyoxymethylene), poly(ethylene naphthalenedicarboxylate), or other blends or copolymers such as poly(ethylene/1,4-cyclohexylenedimethylene terephthalate) PETG or an ionomer.

In another embodiment of the instant invention, the organic material is a resin selected from the group consisting of a thermoset acrylic melamine resin, an acrylic urethane resin, an epoxy carboxy resin, a silane modified acrylic melamine, an acrylic resin with carbamate pendant groups crosslinked with melamine or an acrylic polyol resin crosslinked with melamine containing carbamate groups.

In still other embodiments, the resin is a thermoset acrylic melamine resin or an acrylic urethane resin.

In yet another embodiment of the instant invention, the organic material is a recording material.

The recording materials according to the invention are suitable for pressure-sensitive copying systems, photocopying systems using microcapsules, heat-sensitive copying systems, photographic materials and ink jet printing.

The recording materials according to the invention are distinguished by an unexpected improvement in quality, especially with regard to the fastness to light.

The recording materials according to the invention have the construction known for the particular use. They consist of a customary carrier, for example, paper or plastic film, which has been coated with one or more layers. Depending on the type of material, these layers contain the appropriate necessary components, in the case of photographic materials, for example, silver halide emulsions, dye couplers, dyes and the like. Material particularly suitable for ink jet printing has a layer particularly absorptive for ink on a customary carrier. Uncoated paper can also be employed for ink jet printing. In this case the paper acts at the same time as the carrier material and as the ink-absorbent layer. Suitable material for ink jet printing is, for example, described in U.S. Pat. No. 5,073,448 which is incorporated herein by reference.

The recording material can also be transparent as, for example, in the case of projection films.

The compounds of formula I or II can be incorporated into the carder material as early as the production of the latter, in the production of paper, for example, being added to the paper pulp. A second method of application is to spray the carder material with an aqueous solution of compounds of formula I or II or to add the compounds to the coating composition.

Coating compositions intended for transparent recording materials suitable for projection cannot contain any particles which scatter light, such as pigments and fillers.

The dye-binding coating composition can contain a number of other additives, for example, antioxidants, light stabilizers (including also UV absorbers which do not fall under the scope of the UV absorbers of this invention), viscosity improvers, fluorescent brighteners, biocides and/or antistatic agents.

The coating composition is usually prepared as follows: the water-soluble components, for example, the binder, are dissolved in water and stirred together; the solid components, for example, fillers and other additives already described, are dispersed in this aqueous medium; and disperison is advantageously carried out by means of devices, for example, ultrasonic systems, turbine stirrers, homogenizers, colloid mills, bead mills, sand mills, high-speed stirrers and the like. The compounds of formula I or II can be easily incorporated into the coating composition.

The recording material according to this invention preferably contains 1 to 5000 mg/m$^2$, in particular 50–1200 mg/m$^2$, of a compound of formula I or II.

As already mentioned, the recording materials according to the invention embrace a wide field. The compounds of formula I or II can, for example, be employed in pressure-sensitive copying systems. They can be introduced either into the paper in order to protect the microencapsulated dye precursors there from light, or into the binder of the developer layer in order to protect the dyes formed there.

Photocopying systems using light-sensitive microcapsules which are developed by means of pressure are described in U.S. Pat. Nos. 4,416,966; 4,483,912; 4,352,200; 4,535,050; 4,535,463; 4,551,407; 4,562,137 and 4,608,330; and also in EP-A 139,479; EP-A 162,664; EP-A 164,931; EP-A 237,024; EP-A 237,025 and EP-A 260,129. In all these systems, the compounds can be put into the dye-receiving layer. The compounds can, however, also be put into the donor layer in order to protect the color formers from light.

Photographic materials which can be stabilized are photographic dyes and layers containing such dyes or precursors thereof, for example, photographic paper and films. Suitable materials are, for example, described in U.S. Pat. No. 5,364,749 which is incorporated herein by reference. The compounds of formula I or II act here as a UV filter against electrostatic flashes. In color photographic materials, couplers and dyes are also protected against photochemical decomposition.

The instant compounds can be used for all types of color photographic materials. For example, they can be employed for color paper, color reversal paper, direct-positive color material, color negative film, color positive film, color reversal film and the like. They are preferably used inter alia for photographic color material which contains a reversal substrate or form positives.

Color-photographic recording materials usually contain, on a support, a blue-sensitive and/or a green-sensitive and/or a red-sensitive silver halide emulsion layer and, if desired, a protection layer, with the instant compounds being, preferably, either in the green-sensitive or the red-sensitive layer or in a layer between the green-sensitive and the red-sensitive layer or in a layer on top of the silver halide emulsion layers.

The compounds of formula I or II can also be employed in recording materials based on the principles of photopolymerization, photoplasticization or the rupture of microcapsules, or in cases where heat-sensitive and light-sensitive diazonium salts, leuko dyes having an oxidizing agent or dye lactones having Lewis acids are used.

Furthermore, the instant compounds can be employed in recording materials for dye diffusion transfer printing, thermal wax transfer printing and non-matrix printing and for use with electrostatic, electrographic, electrophoretic, magnetographic and laser-electrophotographic printers and penplotters. Of the above, recording materials for dye diffusion transfer printing are preferred, for example, as described in EP-A 507,734.

The instant compounds can also be employed in inks, such as for ink jet printing, for example, as described in U.S. Pat. No. 5,098,477 which is incorporated herein by reference.

The instant compounds also are effective in the protection of dyes present in candle wax from premature degradation and fading.

The instant compounds of formula I or II are also useful in adhesives used in solar films, optical films and other laminated structures against the adverse effects of ultraviolet light and actinic radiation.

The compounds of this invention exhibit superior hydrolytic stability, handling and storage stability as well as good resistance to extractability when present in a stabilized composition.

The methodology to make the instant compounds is described in the prior art. The intermediates needed to make the instant compounds are largely items of commerce.

In general polymers which can be stabilized include
1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:
 a) radical polymerisation (normally under high pressure and at elevated temperature).
 b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer, and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylontrile (or methacrylonitrile)

on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated PVC, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

31. Polysiloxanes such as the soft, hydrophilic polysiloxanes described, for example, in U.S. Pat. No. 4,259,467; and the hard polyorganosiloxanes described, for example, in U.S. Pat. No. 4,355,147.

32. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

33. Radiation curable compositions containing ethylenically unsaturated monomers or oligomers and a polyunsaturated aliphatic oligomer.

34. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.05 to about 3%, and especially 0.05 to about 1%. However, some high performance films or in UV absorbing layers of laminates such as those produced by coextrusion may contain from 5–15% by weight of the instant compounds. Concentrations of 5–10% by weight are typical in certain coextrusion applications.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants
1.1. Alkylated Monophenols, for Example,
2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol
1.2. Alkylated Hydroquinones, for Example,
2,6-di-tert-butyl-4-methoxyphenol
2,5-di-tert-butyl-hydroquinone
2,5-di-tert-amyl-hydroquinone
2,6-diphenyl-4-octadecyloxyphenol
1.3. Hydroxylated Thiodiphenyl Ethers, for Example,
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)
1.4. Alkylidene-bisphenols, for Example,
2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl)-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl]terephthalate.
1.5. Benzyl Compounds, for Example,
1,3,5-tri-(3,5-di-tert-butyl-4-hydroxybenzyl)-2,4,6-trimethylbenzene
di-(3,5-di-tert-butyl-4-hydroxybenzyl)sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl)isocyanurate
1,3,5-tris-(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt
1.6. Acylaminophenols, for Example,
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate
1.7. Esters of β-(3,5-di-tert-butyl-4-hydroxyphenyl)-propionic Acid with Monohydric or Polyhydric Alcohols, for Example

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |
| triethanolamine | triisopropanolamine |

1.8. Esters of β-(5-tert-butyl-4-hydroxy-3-methylphenyl)-propionic Acid with Monohydric or Polyhydric Alcohols, for Example

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |
| triethanolamine | triisopropanolamine |

1.9. Amides of β-(3,5-di-tert-butyl-4-hydroxyphenyl)-propionic Acid for Example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine
1.10 Diarylamines, for Example,
diphenylamine, N-phenyl-1-naphthylamine, N-(4-tert-octylphenyl)-1-naphthylamine,
4,4'-di-tert-octyl-diphenylamine, reaction product of N-phenylbenzylamine and
2,4,4-trimethylpentene, reaction product of diphenylamine and 2,4,4-trimethylpentene, reaction product of N-phenyl-1-naphthylamine and 2,4,4-trimethylpentene.

2. UV Absorbers and Light Stabilizers 2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxy-octa-(ethyleneoxy)carbonyl-ethyl)-, 3'-dodecyl-5'-methyl-, and 3'-tert-butyl-5-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl)sebacate, bis-(1,2,2,6,6-pentamethylpiperidyl)sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1' (1,2-ethanediyl)-bis-(3,3,5,5-tetramethylpiperazinone), bis (1-octyloxy-2,2,6,6-tetramethylpiperidin-4-yl)sebacate, 1-(2-hydroxy-2-methylpropoxy)-4-octadecanoyloxy-2,2,6,6-tetramethylpiperidine.

2.7. Oxalic acid diamides, for example, 4,4'-di-octyloxy-oxanilide, 2,2'-di-octyloxy-5,5'di-tert-butyl-oxanilide, 2,2'-di-dodecyloxy-5,5'-di-tert-butyl-oxanilide, 2-ethoxy-2'-ethyl-oxanilide, N,N'-bis (3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxy-4-(2-hydroxyethoxy)phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl)phosphite, trilauryl phosphite, trioctadecyl phosphite, di-stearyl-pentaerythritol diphosphite, tris-(2,4-di-tert-butylphenyl)phosphite, di-isodecyl-pentaerythritol diphosphite, di-(2,4,6-tri-tert-butylphenyl)-pentaerythritol diphosphite, di-(2,4-di-tert-butyl-6-methylphenyl)-pentaerythritol diphosphite, di-(2,4-di-tert-butylphenyl)pentaerythritol diphosphite, tristearyl-sorbitol triphosphite, tetrakis-(2,4-di-tert-butylphenyl) 4,4'-diphenylylenediphosphonite.

5. Compounds which destroy Peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

13. Benzofuranones and indolinones, for example those disclosed in U.S. Pat. No. 4,325,863, U.S. Pat. No. 4,338,244 or U.S. Pat. No. 5,175,312, or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl) benzofuran-2-one], 5,7-di-tert-butyl-3-(4-ethoxyphenyl)-benzofuran-2-one, 3-(4-acetoxy-3,5-dimethylphenyl)-5,7-di-tert-butyl-benzofuran-2-one, 3-(3,5-methyl-4-pivaloyloxyphenyl)-5,7-di-tert-butyl-benzofuran-2-one.

The co-stabilizers, with the exception of the benzofuranones listed under 13, are added for example in concentrations of 0.01 to 10%, relative to the total weight of the material to be stabilized.

Further preferred compositions comprise, in addition to components (a) and (b) further additives, in particular phenolic antioxidants, light stabilizers or processing stabilizers.

Particularly preferred additives are phenolic antioxidants (item 1 of the list), sterically hindered amines (item 2.6 of the list), phosphites and phosphonites (item 4 of the list), UV absorbers (item 2 of the list) and peroxide-destroying compounds (item 5 of the list).

Additional additives (stabilizers) which are also particularly preferred are benzofuran-2-ones, such as described, for example, in U.S. Pat. No. 4,325,863, U.S. Pat. No. 4,338,244 or U.S. Pat. No. 5,175,312.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinammate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl) benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3,-tris(2-methyl-4-hydroxy-5-tert-butylphenyl)butane, 1,3,5-tris[2-(3,5-di-tert-butyl-4-hydroxyhydrocinnamoyloxy) ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

The hindered amine compound of particular interest is selected from the group consisting of bis(2,2,6,6-tetramethylpiperidin-4-yl)sebacate, bis(1,2,2,6,6-pentamethylpiperidin-4-yl)sebacate, di(1,2,2,6,6-pentamethylpiperidin-4-yl) (3,5-di-tert-butyl-4-hydroxybenzyl)butylmalonate, 4-benzoyl-2,2,6,6-tetramethylpiperidine, 4-stearoyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl)nitrilotriacetate, 1,2-bis(2,2,6,6-tetramethyl-3-oxopiperazin-4-yl)ethane, 2,2,4,4-tetramethyl-7-oxa-3,20-diaza-2]-oxodispiro[5.1.11.2] heneicosane, polycondensation product of 2,4-dichloro-6-tert-octylamino-s-triazine and 4,4'-hexamethylenebis (amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N'',N'''-tetrakis[(4,6-bis(butyl-1,2,2,6,6-pentamethylpiperidin-4-yl)-amino-s-triazin-2-yl]-1,10-diamino-4,7-diazadecane, mixed [2,2,6,6-tetramethylpiperidin-4-yl/β,β,β',β'-tetramethyl-3,9-(2,4,8,10-tetraoxaspiro[5.5]-undecane)diethyl] 1,2,3,4-butanetetracarboxylate, mixed [1,2,2,6,6-pentamethylpiperidin-4-yl/β,β,β',β'-tetramethyl-3,9-(2,4,8,10-tetraoxaspiro[5.5]-undecane)diethyl] 1,2,3,4-butanetetracarboxylate, octamethylene bis(2,2,6,6-tetramethylpiperidin-4-carboxylate), 4,4'-ethylenebis(2,2,6,6-tetramethylpiperazin-3-one), N-2,2,6,6-tetramethylpiperidin-4-yl-n-dodecylsuccinimide, N-1,2,2,6,6-pentamethylpiperidin-4-yl-n-dodecylsuccinimide, N-1-acetyl-2,2,6,6-tetramethylpiperidin-4-yln-dodecylsuccinimide, 1-acetyl 3-dodecyl-7,7,9,9-tetramethyl-1,3,8-triazaspiro[4.5]decane-2,4-dione, di-(1-octyloxy-2,2,6,6-tetramethylpiperidin-4-yl)sebacate, di-(1-cyclohexyloxy-2,2,6,6-tetramethylpiperidin-4-yl)succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino], 2,4,6-tris[N-(1-cyclohexyloxy-2,2,6,6-tetramethylpiperidin-4-yl)-n-butylamino]-s-triazine, bis[1-(2-hydroxy-2-methylpropoxy)-2,2,6,6-tetramethylpiperidin-4-yl)] sebacate; a mixture of bis[1-(2-hydroxy-2-methylpropoxy)-2,2,6,6-tetramethylpiperidin-4-yl]glutarate and bis[1-(2-hydroxy-2-methylpropoxy)-2,2,6,6-tetramethylpiperidin-4-yl]adipate; 1-(2-hydroxy-2-methyl-propoxy)-4-octadecanoyloxy-2,2,6,6-tetramethylpiperidine; bis[1-(2-hydroxy-2-methylpropoxy)-2,2,6,6-tetramethylpiperidin-4-yl]adipate; bis[1-(2-hydroxy-2-methylpropoxy)-2,2,6,6-tetramethyl-piperidin-4-yl]glutarate; bis[1-(2-hydroxy-2-methylpropoxy)-2,2,6,6-tetramethylpiperidin-4-yl] succinate; a mixture of bis 1-(2-hydroxy-2-methylpropoxy)-2,2,6,6-tetramethylpiperidin-4-yl]glutarate and bis[1-(2-hydroxy-2-methylpropoxy)-2,2,6,6-tetramethylpiperidin-4-yl] succinate; 1-(4-octadecanoyloxy-2,2,6,6-tetramethylpiperidin-1-yloxy)-2-octadecanoyloxy-2-methylpropane; 1-(2-hydroxy-2-methylpropoxy)-4-[9-(methoxy-carbonyl)nonanoyloxy]-2,2,6,6-tetramethylpiperidine; 1-(2-hydroxy-2-methylpropoxy)-4-[5-(methoxy-carbonyl)pentanoyloxy]-2,2,6,6-tetramethylpiperidine; 1-(2-hydroxy-2-methylpropoxy)-4-[3-(methoxy-carbonyl)propionyloxy]-2,2,6,6-tetramethylpiperidine; 1-(2-hydroxy-2-methylpropoxy)-4-[4-(methoxy-carbonyl)-butyryloxy]-2,2,6,6-tetramethylpiperidine; condensation product of 4-hydroxy-1-(2-hydroxy-2-methylpropoxy)-2,2,6,6-tetramethylpiperidine with hexamethylene diisocyanate and terminated with methoxy; condensation product of 4-hydroxy-1-(2-hydroxy-ethoxy)-2,2,6,6-tetramethylpiperidine with hexamethylene diisocyanate and terminated with methoxy; and the condensation product of 4-hydroxy-1-(2-hydroxy-1-phenethoxy)-2,2,6,6-tetramethylpiperidine with hexamethylene diisocyanate and terminated with methoxy.

A most preferred hindered amine compound is bis(2,2,6,6-tetramethylpiperidin-4-yl)sebacate, bis(1,2,2,6,6-pentamethylpiperidin-4-yl)sebacate, di(1,2,2,6,6-pentamethylpiperidin-4-yl) (3,5-di-tert-butyl-4-hydroxybenzyl)butylmalonate, the polycondensation product of 1-(2-hydroxyethyl)-2,2,6,6-tetramethyl-4-hydroxypiperidine and succinic acid, the polycondensation product of 2,4-dichloro-6-tert-octylamino-s-triazine and 4,4'-hexamethylenebis(amino-2,2,6,6-tetramethylpiperidine), N,N',N'',N'''-tetrakis[(4,6-bis(butyl-(1,2,2,6,6-pentamethylpiperidin-4-yl)amino)-s-triazine-2-yl]-1,10-diamino-4,7-diazadecane.di-(1-octyloxy-2,2,6,6-tetramethylpiperidin-4-yl)sebacate, di-(1-cyclohexyloxy-2,2,6,6-tetramethylpiperidin-4-yl)succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6-tetramethylpiperidin-4-yl)imino-hexamethylene-[4-(1-cyclohexyloxy-2,2,6,6-tetramethylpiperidin-4-yl)imino], 2,4,6-tris[N-(1-cyclohexyloxy-2,2,6,6-tetramethylpiperidin-4-yl)-n-butylamino]-s-triazine, or 1-(2-hydroxy-2-methylpropoxy)-4-octadecanoyloxy-2,2,6,6-tetramethypiperidine.

The instant composition can additionally contain another UV absorber selected from the group consisting of the benzotriazoles, the s-triazines, the oxanilides, the salicylates, the hydroxybenzophenones, the benzoates and the α-cyanoacrylates.

Particularly, the instant composition may additionally contain an effective stabilizing amount of at least one other 2-hydroxyphenyl-2H-benzotriazole; another tris-aryl-s-triazine; or hindered amine or mixtures thereof.

Preferably, the 2-hydroxypheny-2H-benzotriazole is selected from the group consisting of
2-(2-hydroxy-3,5-di-tert-amylphenyl)-2H-benzotriazole;
2-[2-hydroxy-3,5-di(α,α-dimethylbenzyl)phenyl]-2H-benzotriazole;
2-[2-hydroxy-3-(α,α-dimethylbenzyl)-5-tert-octylphenyl]-2H-benzotriazole;
2-{2-hydroxy-3-tert-butyl-5-[2-(omega-hydroxy-octa (ethyleneoxy)carbonyl)ethyl]phenyl}-2H-benzotriazole;
5-chloro-2-(2-hydroxy-3,5-di-tert-butylphenyl)-2H-benzotriazole;
5-chloro-2-(2-hydroxy-3-tert-butyl-5-methylphenyl)-2H-benzotriazole;
2-(2-hydroxy-5-tert-octylphenyl)-2H-benzotriazole; and
2-{2-hydroxy-3-tert-butyl-5-[2-(octyloxy)carbonyl)ethyl]phenyl}-2H-benzotriazole.

Preferably, the other tris-aryl-s-triazine is selected from the group consisting of
2,4-bis(2,4-dimethylphenyl)-6-(2-hydroxy-4-octyloxyphenyl)-s-triazine;
2,4-diphenyl-6-(2-hydroxy-4-hexyloxyphenyl)-s-triazine;
2,4-bis(2,4-dimethylphenyl)-6-[2-hydroxy-4-(3-do-/tridecyloxy-2-hydroxypropoxy)-phenyl]-s-triazine;
2,4-bis(2,4-dimethylphenyl)-6-[2-hydroxy-4-(3-nonyloxy*-2-hydroxy-propyloxy)-5-α-cumylphenyl]-s-triazine. (* denotes a mixture of octyloxy, nonyloxy and decyloxy groups.), and
2,4-bis(biphenylyl)-6-[2-hydroxy-4-(3-nonyloxy*-2-hydroxypropyloxy)phenyl]-s-triazine. (* denotes a mixture of octyloxy, nonyloxy and decyloxy groups.)

The instant compounds are often used in conjunction with one or more coadditive stabilizers where the coadditive stabilizer is a hindered phenolic antioxidant selected from the group consisting of neopentanetetrayl tetrakis(3,5-di-tert-butyl-4-hydroxyhydrocinnamate, octadecyl 3,5-di-tert-butyl-4-hydroxyhydrocinnamate, 1,3,5-trimethyl-2,4,6-tris (3,5,-di-tert-butyl-4-hydroxybenzyl)benzene, 1,2-bis(3,5-di-tert-butyl-4-hydroxyhydrocinnamoyl)hydrazine, calcium [bis(monoethyl 3,5-ditert-butyl-4-hydroxybenzyl)-phosphonate], 1,3,5-tris(3,5-di-tert-butyl-4-hydroxybenzyl) isocyanurate and 1,3,5-tris(3-hydroxy-4-tert-butyl-2,6-dimethylbenzyl)isocyanurate; or is an organophosphorus stabilizer selected from the group consisting of tris(2,4-di-tert-butylphenyl)phosphite, bis(2,4-di-tert-butyl-6-methylphenyl)ethyl phosphite, 2,2',2''-nitrilo[triethyl-tris-(3,3',5,5'-tetra-tert-butyl-1,1'-biphenyl-2,2'-diyl)phosphite], tetrakis(2,4-di-butylphenyl) 4,4'-biphenylenediphosphonite, tris(nonylphenyl)phosphite, bis(2,4-di-tert-butylphenyl) pentaerythrityl diphosphite, 2,2'-ethylidenebis(2,4-di-tert-butylphenyl)fluorophosphite and 2-butyl-2-ethylpropan-1,3-diyl 2,4,6-tri-tert-butylphenyl phosphite; or is 5,7-di-tert-butyl-3-(3,4-dimethylphenyl)-2H-benzofuran-2-one; or is N,N-dialkylhydroxylamine made by the direct oxidation of N,N-di(hydrogenated tallow)amine; or is a hindered amine selected from the group consisting of bis(2,2,6,6-tetramethylpiperidin-4-yl)sebacate, the polycondensation product of 1-(2-hydroxyethyl)-2,2,6,6-tetramethyl-4-hydroxypiperidine and succinic acid, N,N',N'',N'''-tetrakis[4,6-bis(butyl-1,2,2,6,6-penta-methylpiperidin-4-yl)amino-s-triazin-2-yl]-1,10-diamino-4,7-diazadecane, the polycondensation product of 4,4'-hexamethylenebis(amino-2,2,6,6-tetramethylpiperidine) and 2,4-dichloro-6-tert-octylamino-s-triazine, the polycondensation product of 4,4'-hexamethylenebis(amino-2,2,6,6-tetramethylpiperidine) and 2,4-dichloro-6-morpholino-s-triazine, the polycondensation product of 4,4'-hexamethylenebis(amino-1,2,2,6,6-pentamethylpiperidine) and 2,4-dichloro-6-morpholino-s-triazine, 2,2,6,6-tetramethylpiperidin-4-yl octadecanoate, 3-dodecyl-1-(1-acetyl-2,2,6,6-tetramethylpiperidin-4-yl)-pyrrolidin-2,5-dione, 1,3,5-tris[N-cyclohexyl-N-[2-(2,2,6,6-tetramethylpiperazin-3-on-4-yl)ethyl]amino]-s-triazine, poly[methyl 3-(2,2,6,6-tetramethylpiperidin-4-yloxy)-propyl]siloxane, the polycondensation product of 2,4-dichloro-6-(2,2,6,6-tetramethylpiperidin-4-yl)butylamino)-s-triazine, 2,2'ethylene-bis{[2,4-(2,2,6,6-tetramethylpiperidin-4-yl)butylamino-s-triazin-6-yl] aminotrimethyleneamino}, oligomer of N-{[2-(N-2,2,6,6-tetramethylpiperidin-4-yl}butylamino]-s-triazin-4-yl}-N,N'-bis(2,2,6,6-tetramethylpiperidin-4-yl)-1,6-hexanediamine terminated with 2,4-bis(dibutylamino)-s-triazin-6-yl, N,N',N'''-tris{2,4-bis[N-(1,2,2,6,6-pentamethylpipedidin-4-yl)butylamino]-s-triazin-6-yl}-3,3'-ethylenediiminodipropylamine, N,N',N'''-tris{2,4-bis[N-(1,2,2,6,6-pentamethylpiperidin-4-yl)butylamino]-s-triazin-6-yl}-3,3'-ethylenediiminodipropylamine and N,N'N''N,N'''-tetrakis{2,4-bis[N-(1,2,2,6,6-pentamethylpiperidin-4-yl) butylamino]-s-triazin-6-yl}-3,3'-ethylenediiminodipropylamine; or is another N-hydrocarbyloxy substituted hindered amines selected from the group consisting of bis(1-octyloxy-2,2,6,6-tetramethylpiperidin-4-yl)sebacate, bis(1-octyloxy-2,2,6,6-tetramethylpiperidin-4-yl)adipate, bis(1-cyclohexyloxy-2,2,6,6-tetramethylpiperidin-4-yl)adipate, bis(1-cyclohexyloxy-2,2,6,6-tetramethylpiperidin-4-yl)sebacate, 1-cyclohexyloxy-2,2,6,6-tetramethylpiperidin-4-yl octadecanoate, N,N',N''-tris{2,4-bis[N-(1-cyclohexyloxy-2,2,6,6-tetramethylpiperidin-4-yl)butylamino]-s-triazin-6-yl}-3,3'-ethylenediiminodipropylamine, N,N',N'''-tris{2,4-bis[N-(1-cyclohexyloxy-2,2,6,6-tetramethylpiperidin-4-yl)butylamino]-s-triazin-6-yl}-3,3'-ethylenediiminodipropylamine and N,N',N'',N'''-tetrakis{2,4-bis[N-(1-cyclohexyloxy-2,2,6,6-tetramethylpiperidin-4-yl)butylamino]-s-triazin-6-yl}-3,3'-ethylenediiminodipropylamine; or a hydroxy substituted N-hydrocarbyloxy substituted hindered amine selected from the group consisting of bis[1-(2-hydroxy-2-methylpropoxy)-2,2,6,6-tetramethylpiperidin-4-yl)] sebacate; a mixture of bis[1-(2-hydroxy-2-methylpropoxy)-2,2,6,6-tetramethylpiperidin-4-yl]glutarate and bis[1-(2-hydroxy-2-methylpropoxy)-2,2,6,6-tetramethylpiperidin-4-yl]adipate; 1-(2-hydroxy-2-methylpropoxy)-4-octadecanoyloxy-2,2,6,6-tetramethylpiperidine; bis[1-(2-hydroxy-2-methylpropoxy)-2,2,6,6-tetramethylpiperidin-4-yl]adipate; bis[1-(2-hydroxy-2-methylpropoxy)-2,2,6,6-tetramethylpiperidin-4-yl]glutarate; bis[1-(2-hydroxy-2-methylpropoxy)-2,2,6,6-tetramethylpiperidin-4-yl]succinate; a mixture of bis[1-(2-hydroxy-2-methylpropoxy)-2,2,6,6-tetramethylpiperidin-4-yl]glutarate and bis[1-(2-hydroxy-2-methylpropoxy)-2,2,6,6-tetramethylpiperidin-4-yl]succinate; 1-(4-octadecanoyloxy-2,2,6,6-tetramethylpiperidin-1-yloxy)-2-octadecanoyl-oxy-2-methylpropane; 1-(2-hydroxy-2-methylpropoxy)-4-[9-(methoxy-carbonyl)nonanoyloxy]-2,2,6,6-tetramethylpiperidine; 1-(2-hydroxy-2-methylpropoxy)-4-[5-(methoxy-carbonyl)pentanoyloxy]-2,2,6,6-tetramethylpiperidine; 1-(2-hydroxy-2-methylpropoxy)-4-[3-(methoxy-carbonyl)propionyloxy]-2,2,6,6-tetramethylpiperidine; 1-(2-hydroxy-2-methylpropoxy)-4-[4-(methoxy-carbonyl)butyryloxy]-2,2,6,6-tetramethylpiperidine; or is a UV absorber selected from the group consisting of 2-(2-hydroxy-3,5-di-α-cumylphenyl)-2H-benzotriazole, 2-(2-hydroxy-5-methylphenyl)-2H-benzotriazole, 5-chloro-2-(2-hydroxy-3,5-di-tert-butylphenyl)-2H-benzotriazole, 2-(2-hydroxy-3,5-di-tert-amylphenyl)-2H-benzotriazole, 2-(2-hydroxy-3-α-cumyl-5-tert-octylphenyl)-2H-benzotriazole, 2,4-di-tert-butylphenyl 3,5-di-tert-butyl 4-hydroxybenzoate, 2-hydroxy-4-n-octyloxybenzophenone, 2,4-bis(2,4-dimethyphenyl)-6-(2-hydroxy-4-octyloxyphenyl)-s-triazine, oligomer of N-{2-[(1-propoxy-2,2,6,6-tetramethylpiperidin-4-yl)butylamino]-s-triazin-4-yl}-N,N'-bis(1-propoxy-2,2,6,6-tetramethylpiperidin-4-yl)-1,6-hexanediamine terminated with 2,4-bis(dibutylamino)-s-triazin-6-yl, the condensation product of 2-morpholino-4,6-dichloro-s-triazine with N,N'-bis(1,2,2,6,6-pentamethylpiperidin-4-yl)-1,6-hexanediamine; or mixtures thereof Preferably the coadditive stabilizer is neopentanetetrayl tetrakis(3,5-di-tert-butyl-4-hydroxyhydrocinnamate, tris(2,4-di-tert-butylphenyl)phosphite, N,N-dialkylhydroxylamine made by the direct oxidation of N,N-di(hydrogenated tallow)amine, N,N',N'',N'''-tetrakis[4,6-bis(butyl-1,2,2,6,6-pentamethylpiperidin-4-yl)amino-s-triazin-2-yl]-1,10-diamino-4,7-diazadecane, the polycondensation product of 4,4'-hexamethylenebis(amino-2,2,6,6-tetramethylpiperidine) and 2,4-dichloro-6-tert-octylamino-s-triazine, the polycondensation product of 4,4'-hexamethylenebis(amino-2,2,6,6-tetramethylpiperidine) and 2,4-dichloro-6-morpholino-s-triazine, the polycondensation product of 4,4'-hexamethylenebis(amino-1,2,2,6,6-pentamethylpiperidine) and 2,4-dichloro-6-morpholino-s-triazine, oligomer of N-{[2-(N-2,2,6,6-tetramethylpiperidin-4-yl)butylamino]-s-triazin-4-yl}-N,N'-bis(2,2,6,6-tetramethylpiperidin-4-yl)-1,6-hexanediamine terminated with 2,4-bis(dibutylamino)-s-triazin-6-yl, N,N',N''-tris{2,4-bis[N-(1,2,2,6,6-pentamethylpiperidin-4-yl)butylamino]-s-triazin-6-yl}-3,3'-ethylenediiminodipropylamine, N,N',N'''-tris{2,4-bis[N-(1,2,2,6,6-pentamethylpiperidin-4-yl)butylamino]-s-triazin-6-yl}-3,3'-ethylenediiminodipropylamine and N,N',N'',N'''-tetrakis{2,4-bis[N-(1,2,2,6,6-penta-methylpiperidin-4-yl)butylamino]-s-triazin-6-yl}-3,3'-ethylenediiminodipropylamine, oligomer of N-{2-[(1-propoxy-2,2,6,6-tetramethylpiperidin-4-yl)butylamino]-s-triazin-4-yl}-N,N'-bis(1-propoxy-2,2,6,6-tetramethylpiperidin-4-yl)-1,6-hexanediamine terminated with 2,4-bis(dibutylamino)-s-triazin-6-yl, or the condensation product of 2-morpholino-4,6-dichloro-s-triazine with N,N'-bis(1,2,2,6,6-pentamethylpiperidin-4-yl)-1,6-hexanediamine.

The alkyd resin lacquers which can be stabilized against the action of light and moisture in accordance with the instant invention are the conventional stoving lacquers which are used in particular for coating automobiles (automobile finishing lacquers), for example lacquers based on alkyd/melamine resins and alkyd/acrylic/melamine resins (see H. Wagner and H. F. Sarx, "Lackkunstharze" (1977), pages 99–123). Other crosslinking agents include glycouril resins, blocked isocyanates or epoxy resins.

The lacquers stabilized in accordance with the invention are suitable both for metal finish coatings and solid shade finishes, especially in the case of retouching finishes, as well as various coil coating applications. The lacquers stabilized in accordance with the invention are preferably applied in the conventional manner by two methods, either by the single-coat method or by the two-coat method. In the latter method, the pigment-containing base coat is applied first and then a covering coat of clear lacquer over it.

It is also to be noted that the compounds of the present invention are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anhydrides, amines and the like. Correspondingly, the epoxide may be utilized as the crosslinking agent for various acrylic or polyester resin systems that have been modified by the presence of reactive groups on the backbone structure.

When used in two-coat finishes, the compounds of the instant invention can be incorporated in the clear coat or both in the clear coat and in the pigmented base coat.

When water-soluble, water miscible or water dispersible coating are desired ammonium salts of acid groups present in the resin are formed. Powder coating composition can be prepared by reacting glycidyl methacrylate with selected alcohol components.

The instant benzotriazoles are made by conventional methods for preparing such compounds. The usual procedure involves the diazotization of a substituted o-nitroaniline followed by coupling the resultant diazonium salt with a substituted phenol and reduction of the azobenzene intermediate to the corresponding desired benzotriazole. The starting materials for these benzotriazoles are largely items of commerce or can be prepared by normal methods of organic synthesis.

While the instant benzotriazoles with their enhanced durability are particularly suited for automotive coating applications, it is contemplated that they will also be espeically useful in other applications where their enhanced durability is required such as in solar films and the like.

The instant invention also pertains to candle wax compositions which comprises (a) white and unscented, white and scented, dyed and unscented, dyed and scented, dipped and unscented or dipped and scented candle wax, and (b) an effective stabilizing amount of a benzoniazole of formula I or II as described above alone or in combination with a hindered amine.

An effective amount of benzotriazole alone or plus the hindered amine in the candle wax is 0.01 to 10% by weight, preferably 0.1 to 2% by weight; and most preferably 0.1 to 0.5% by weight based on the wax. When a combination of benzotriazole and hindered amine are used, the weight ratio of benzotriazole to hindered amine is 10:1 to 1:10, preferably 4:1 to 1:4; most preferably 2:1 to 1:2 based on the candle wax.

It should be noted that candles contain a host of various components. The base materials may be made up of the following:

paraffin wax,
natural oils,
polyamide plus fatty acid/ester,
fatty acids such as stearin,
opacifiers,
beeswax,
glycerides plus oxidized wax,
alcohols, and
ethylene oligomers.

Candles also contain a number of additives such as the following:

mold release agents,
fragrances,
insect repellants or insecticides,
hardeners,
crystal modifiers,
clarifiers,
guttering reducers,
colorants,
f.p. control agents,
stretchability improvers,
gelling agents,
extrusion aids, and
vortex reducers.

Each of the various components are meant to control or modify the properties of the candle to insure proper burning, reduce channelling, aid in uniform melting, and the like. The colorants and fragrances obviously are there to provide the proper color, scent or other aesthetic appeal.

Of increasing importance are the transparent gel candles which look like clear glass, but which burn like a classical candle. As is discussed in detail in U.S. Pat. No. 5,879,694, the relevant parts of which are incorporated herein by reference, these gel candles usually contain a copolymer selected from the group consisting of a triblock, radial block, diblock or multiblock copolymer classically made up of at least two thermodynamically incompatible segments containing both hard and soft segments. Typical of such block copolymers is KRATON® (Shell Chemical Co.) which consists of block segments of styrene monomer units and rubber monomer or comonomer units. The most common structure found in KRATON® D series is a linear ABA block with styrene-butadiene-styrene (SBS) or styrene-isoprene-styrene (SIS).

Candles may also contain other stabilizers such as phenolic antioxidants, phosphites, hydroxylamines and the like, particularly phenolic antioxidants such as are described above.

The following examples are for illustrative purposes only and are not to be construed to limit the scope of the instant invention in any manner whatsoever.

EXAMPLE 1

5-Phenyl-2-(2-hydroxy-3-phenyl-5-tert-octylphenyl)-2H-benzotriazole (A) 3-Nitro-4-acetamido-1,1'-biphenyl To a mixture of 4-acetamido-1,1'-biphenyl (21.1 g, 0.1 mol) and 150 mL of acetic anhydride maintained between 8° C. and 13° C. is slowly added dropwise over 32 minutes 12.7 mL of 70% nitric acid. The reaction mixture is added to 600 mL of a mixture of water and ice and the resultant precipitate is collected by filtration. The filter cake is washed with water and the residue is recrystallized from methanol (800 mL) to give 23.6 g of the title compound as a yellow crystalline solid melting at 129–132° C.

(B) 3-Nitro-4-amino-1,1'-biphenyl

A mixture of potassium hydroxide (2.5 g), 3-nitro-4-acetamido-1,1'-biphenyl (23.5 g), prepared in (A) above, water (6 mL) and ethanol (12 mL) is heated at reflux for one hour. The reaction mixture is cooled to room temperature and then poured into 300 mL of a mixture of water and ice. The solid is collected by filtration and the crude product is recrystallized from methanol (800 mL) to give 14.1 g of the title compound as an orange solid melting at 170–17° C.

(C) 4-Phenyl-2-nitrobenzenediazonium Hydrogen Sulfate

To 70 mL of sulfuric acid at 100° C. is added portionwise sodium nitrite (7 g, 0.1 mol). The reaction mixture is warmed to 20° C. to dissolve all the sodium nitrite and then cooled to 15° C. To the reaction mixture is added over 30 minutes a suspension of 3-nitro-4-amino-1,1'-biphenyl (7.33 g, 0.034 mol), prepared in (B) above, in 60 mL of acetic acid. The reaction mixture is stirred for one hour at 100° C. and then to the reaction mixture is added 500 mL of diethyl ether. An exotherm occurs. The mixture is stirred for one hour. The solid formed is removed by filtration behind a safety shield and washed with diethyl ether to give 16.2 g of the title compound as a yellow solid. The solidis dried for 1.5 hours at 20° C. under vacuum and stored in a freezer in a polyethylene container until later use. Analysis: IR (nujol) v 1650 (N=N), 2250 ($N_2^+$) $cm^{-1}$.

(D) 2-Hydroxy-2'nitro-3,4'-diphenyl-5-tert-octylazobenzene

To a solution of sodium hydroxide (12 g, 0.3 mol) and 2-phenyl-4-tert-octylphenol (14.1 g, 0.05 mol) in 150 mL of methanol maintained at 0–5° C. is added portionwise over 1.25 hours 4-phenyl-2-nitrobenzenediazonium hydrogen sulfate (30.6 g, 0.065 mol), prepared in (C) above. The reaction mixture is stirred for two hours at 0–5° C. Xylene (200 mL) is added to the reaction mixture. The organic phase is separated and extracted with water (4×200 mL). The organic phase is filtered and the solvent removed by distillation under an atmosphere of nitrogen. The residue is purified by flash chromatography (90:10 heptane:ethyl acetate eluent) to give 6.56 g of the title compound as a viscous dark red liquid.

(E) 5-Phenyl-2-(2-hydroxy-3-phenyl-5-tert-octylphenyl)-2H-benzotriazole

To a solution of sodium hydroxide (6 g, 0.15 mol) in 8 mL of water is added 2-hydroxy-2'nitro-3,4'-diphenyl-5-tert-octylazobenzene (6.56 g), prepared in (D) above. The reaction mixture is heated to reflux and then formadine sulfinic acid (10.8 g, 0.1 mol) is added portionwise over 20 minutes.

The reaction mixture is heated at reflux for 1.5 hours. To the cooled reaction mixture is added 200 mL of water and the ethanol is removed under vacuum. The reaction mixture is adjusted to pH 4 with hydrochloric acid. The resultant mixture is extracted twice with methylene chloride and the combined organic phases are extracted with water. The organic phase is dried over anhydrous magnesium sulfate, and the solvent is then removed under vacuum. The residue is recrystallized sequentially from a mixture of water and methanol, and petroleum ether to give the title compound as a white solid melting at 123–125° C.

EXAMPLE 2

5-(4-Trifluoromethylphenyl)-2-(2-hydroxy-3-α-cumyl-5-tert-octylphenyl)-2H-benzotriazole This example illustrates the use of n-propanol as solvent and triphenylphosphine as a ligand in the Suzuki reaction to make the instant compound.

A flask, equipped with a mechanical stirrer and an inert atmosphere with a FIRESTONE® valve, containing a mixture of 5-bromo-2-(2-hydroxy-3-α-cumyl-5-tert-octyl)phenyl)-2H-benzotriazole (5.21 g, 0.01 mol), 4-trifluoromethylphenylboronic acid (1.99 g, 0.0105 mol) and 250 mL of n-propanol is evacuated and filled three times with nitrogen. To this mixture is then added palladium(II) diacetate (0.090 g, 0.0004 mol), triphenylphosphine (0.315 g, 0.0012 mol), 6 mL of 2M sodium carbonate (1.27 g, 0.012 mol) and 10 mL of water. The flask is then evacuated and filled with nitrogen three times. The reaction mixture is stirred for 15 minutes at room temperature and then heated to 85° C. The reaction mixture is heated at 85° C. for four hours and then allowed to cool to room temperature. The solvent is removed under vacuum and the residue is partitioned between diethyl ether (250 mL) and water (100 mL). The organic phase is separated and extracted sequentially with 5% aqueous sodium bicarbonate (100 mL) and saturated aqueous sodium chloride (100 mL). The organic phase is dried over anhydrous sodium sulfate and the volatiles are removed under vacuum. The residue is recrystallized from isopropanol (250 mL) to give 3.59 g (61% yield) of a light yellow solid. An analytical sample is prepared by dissolving the product in toluene (25 mL) and treating the resultant solution with activated carbon followed by chromatography (silical gel; ethyl acetate eluent) to give 2.87 g of the title compound as a pale yellow solid. Further purification is effected by sublimation to give a product melting at 146–147.5° C.

$^1$Hnmr (CDCl$_3$; 499.8494 MHz) δ 0.84 (s, 9H); 1.52 (s, 6H); 1.83 (s, 6H); 1.86 (s, 2H); 7.15–7.30 (overlapping multiplets, 5H); 7.65 (d, 1H); 7.69 (d, 1H); 7.77 (multiplet, 4H); 7.96 (d, 1H); 8.05 (d, 1H); 8.36 (d, 1H); 11.33 (s, 1H);

$^{19}$Fnmr (CDCl$_3$; 282.3300 MHz) δ −69.04;

Analysis: Calcd for C$_{36}$H$_{38}$F$_3$N$_3$O: C, 73.82; H, 6.54; N, 7.17. Found: C, 73.82; H, 6,46; N, 7.07.

EXAMPLE 3

5-(4-Trifluoromethylphenyl)-2-(2-hydroxy-3-α-cumyl-5-tert-octylphenyl)-2H-benzotriazole This example illustrates the use of isopropanol as solvent and triphenylphosphine as a ligand in the Suzuki reaction to make the instant compound.

The procedure of Example 2 is followed using 5-bromo-2-(2-hydroxy-3-α-cumyl-5-tert-octyl)phenyl)-2H-benzotriazole (1.04 g, 0.002 mol), 4-trifluoromethylphenylboronic acid (0.40 g, 0.0021 mol), palladium(II) diacetate (0.045 g, 0.0002 mol), triphenylphosphine (0.160 g, 0.0006 mol), 1.2 mL of 2M sodium carbonate (0.25 g, 0.0024 mol), 2 mL of water and 50 mL of isopropanol at 79° C. for five hours to give 0.97 g (83% yield) of the title compound as a solid identical to that prepared in Example 2.

EXAMPLE 4

5-(4-Trifluoromethylphenyl)-2-(2-hydroxy-3-α-cumyl-5-tert-octylphenyl)-2H-benzotriazole This example illustrates the use of dioxane as solvent, 2-(di-tert-butylphosphino)-biphenyl as a ligand, and potassium fluoride in place of sodium carbonate in the Suzuki reaction to make the instant compound.

The procedure of Example 2 is followed using 5-bromo-2-(2-hydroxy-3-α-cumyl-5-tert-octyl)phenyl)-2H-benzotriazole (1.04 g, 0.002 mol), 4-trifluoromethylphenylboronic acid (0.57 g, 0.003 mol), palladium(II) diacetate (0.045 g, 0.0002 mol), 2-(di-tert-butylphosphino)biphenyl (0.119 g, 0.0004 mol), potassium fluoride (0.34 g, 0.0006 mol) and 30 mL of dioxane at 67° C. for 1.25 hours to give 0.46 g (39% yield) of the title compound as a solid identical to that prepared in Example 2.

EXAMPLE 5

5-(4-Trifluoromethylphenyl)-2-(2-hydroxy-3-α-cumyl-5-tert-octylphenyl)-2H-benzotriazole This example illustrates the use of dioxane as solvent, 1,1'-bis[2,4,8,10-tetrakis-(tert-butyl)-dibenzo[d,f][1,3,2]dioxaphosphepin-6-yl]ferrocene as a ligand, and potassium fluoride in place of sodium carbonate in the Suzuki reaction to make the instant compound.

The procedure of Example 2 is followed using 5-bromo-2-(2-hydroxy-3α-cumyl-5-tert-octyl)phenyl)-2H-benzotriazole (1.04 g, 0.002 mol), 4-trifluoromethylphenylboronic acid (0.57 g, 0.003 mol), palladium(II) diacetate (0.045 g, 0.0002 mol), 1,1'-bis[2,4,8,10-tetrakis(tert-butyl)-dibenzo[d,f][1,3,2]dioxaphosphepin-6-yl]ferrocene (0.425 g, 0.0004 mol), potassium fluoride (0.34 g, 0.0006 mol) and 30 mL of dioxane at 67° C. for 1.25 hours to give 0.84 g (72% yield; dry column chromatography; 9:1 heptane:ethyl acetate eluent) of the title compound as a solid identical to that prepared in Example 2.

EXAMPLE 6

5-(3-Trifluoromethylphenyl)-2-(2-hydroxy-3-α-cumyl-5-tert-octylphenyl)-2H-benzotriazole This example illustrates the use of isopropanol as solvent and triphenylphosphine as a ligand in the Suzuki reaction to make the instant compound.

The procedure of Example 2 is followed using 5-bromo-2-(2-hydroxy-3-β-cumyl-5-tert-octyl)phenyl)-2H-benzotriazole (1.04 g, 0.002 mol), 3-trifluoromethylphenylboronic acid (0.40 g, 0.0021 mol), palladium(II) diacetate (0.045 g, 0.0002 mol), triphenylphosphine (0.160 g, 0.0006 mol), 1.2 mL of 2M sodium carbonate (0.25 g, 0.0024 mol), 2 mL of water and 50 mL of isopropanol at 79° C. for five hours. The residue is purified by recrystallization from isopropanol (20 mL) followed by chromatography (acid alumina; 9:1 heptane:ethyl acetate eluent) to give 0.80 g (68% yield) of the title compound as a light yellow solid melting at 138–139.5° C.

¹Hnmr (CDCl₃; 499.8494 MHz) δ 0.81 (s, 9H); 1.52 (s, 6H); 1.83 (s, 6H); 1.86 (s, 2H); 7.15–7.32 (overlapping multiplets, 5H); 7.62 (dd, 1H); 7.64 (d, 1H); 7.67 (d, 1H); 7.69 (dd, 1H); 7.84 (d, 1H); 7.91 (unresolved d, 1H); 7.95 (d, 1H); 8.05 (d, 1H); 8.36 (d, 1H); 11.33 (s, 1H);

¹⁹Fnmr (CDCl₃; 282.3300 MHz) δ −69.04;

MS (DIP) m/z 585 (M⁺)

Analysis: Calcd for $C_{36}H_{38}F_3N_3O$: C, 73.82; H, 6.54; N, 7.17. Found: C, 73.48; H, 6,46; N, 6.92.

EXAMPLE 7

5-(3-Trifluoromethylphenyl)-2-(2-hydroxy-3-α-cumyl-5-tert-octylphenyl)-2H-benzotriazole This example illustrates the use of n-propanol as solvent and triphenylphosphine as a ligand in the Suzuki reaction to make the instant compound.

The procedure of Example 2 is followed using 5-bromo-2-(2-hydroxy-3-α-cumyl-5-tert-octyl)phenyl)-2H-benzotriazole (5.21 g, 0.01 mol), 3-trifluoromethylphenylboronic acid (1.99 g, 0.0105 mol), palladium(II) diacetate (0.090 g, 0.0004 mol), triphenylphosphine (0.315 g, 0.0012 mol), 6 mL of 2M sodium carbonate (1.27 g, 0.012 mol), 10 mL of water and 250 mL of n-propanol at 84° C. for 3.5 hours to give 5.17 g (88% yield) of the title compound as a solid identical to the compound prepared in Example 6.

EXAMPLE 8

5-(2-Trifluoromethylphenyl)-2-(2-hydroxy-3-α-cumyl-5-tert-octylphenyl)-2H-benzotriazole This example illustrates the use of isopropanol as solvent and triphenylphosphine as a ligand in the Suzuki reaction to make the instant compound.

The procedure of Example 2 is followed using 5-bromo-2-(2-hydroxy-3-α-cumyl-5-tert-octyl)phenyl)-2H-benzotriazole (2.60 g, 0.005 mol), 2-trifluoromethylphenylboronic acid (0.997 g, 0.00525 mol), palladium(II) diacetate (0.045 g, 0.0002 mol), triphenylphosphine (0.157 g, 0.0006 mol), 3 mL of 2M sodium carbonate (0.64 g, 0.006 mol), 5 mL of water and 200 mL of n-propanol at 91° C. for two hours. The residue is purified by chromatography (toluene eluent) followed by recrystallization from isopropanol (50 mL) to give 1.85 g (63% yield) of the title compound as a yellow solid melting at 133.5–136° C. ¹Hnmr (CDCl₃; 499.8494 MHz) δ 0.84 (s, 9H); 1.52 (s, 6H); 1.83 (s, 6H); 1.86 (s, 2H); 7.15–7.32 (overlapping multiplets, 5H); 7.40 (overlapping d, 2H); 7.53 (dd, 1H); 7.61 (dd, 1H); 7.64 (d, 1H); 7.80 (multiplet, 2H); 7.88 (d, 1H); 8.36 (d, 1H); 11.35 (s, 1H);

¹⁹Fnmr (CDCl₃; 282.3300 MHz) δ −63.4;

MS (DIP) m/z 585 (M⁺)

EXAMPLE 9

5-Phenyl-2-(2-hydroxy-3-α-cumyl-5-tert-octylphenyl)-2H-benzotriazole (A) 2-Hydroxy-2'nitro-3-α-cumyl-4'-phenyl-5-tert-octylazobenzene The procedure of Example 1 (D) is followed using sodium hydroxide (4 g, 0.1 mol), methanol (100 mL), 4-phenyl-2-nitrobenzenediazonium hydrogen sulfate (16 g, 0.034 mol) and 2-α-cumyl-4-tert-octylphenol (8.1 g, 0.028 mol) to give the title compound as a dark red solid melting at 176–179° C.

(B) 5-Phenyl-2-(2-hydroxy-3-α-cumyl-5-tert-octylphenyl)-2H-benzotriazole

The procedure of Example 1 (E) is followed using sodium hydroxide (4 g, 0.1 mol), 5 mL of water, 2-hydroxy-2'nitro-3-α-cumyl-4'-phenyl-5-tert-octylazobenzene (4 g, 0.0072 mol) and fomamidine sulfinic acid (6.5 g, 0.06 mol) to give the title compound as a pale yellow crystalline solid melting at 137–139° C.

¹Hnmr (CDCl₃) δ 0.84 (s, 9H); 1.52 (s, 6H); 1.83 (s, 6H); 1.86 (s, 2H); 7.15–7.32 (overlapping multiplets, 5H); 7.41 (t, 1H); 7.50 (dd, 2H); 7.63 (d, 1H); 7.67 (d, 2H); 7.71 (dd, 1H); 7.92 (d, 1H); 8.01 (d, 1H); 8.35 9D, 1h); 11.41 (s, 1H).

Analysis: Calcd for $C_{35}H_{39}N_3O$: C, 81.20; H, 7.59; N, 8.12. Found: C, 80.97; H, 7.54; N, 8.07.

EXAMPLE 10

5-Phenyl-2-(2-hydroxy-3-α-cumyl-5-tert-octylphenyl)-2H-benzotriazole

The procedure of Example 2 is followed using 5-bromo-2-(2-hydroxy-3-α-cumyl-5-tert-octyl)phenyl)-2H-benzotriazole (5.21 g, 0.01 mol), phenylboronic acid (1.28 g, 0.0105 mol), palladium(II) diacetate (0.090 g, 0.0004 mol), triphenylphosphine (0.315 g, 0.0012 mol), 6 mL of 2M sodium carbonate (1.27 g, 0.012 mol), 10 mL of water and 250 mL of isopropanol at 84° C. for 3.5 hours. The title compound is obtained as a solid which is identical to that prepared in Example 9.

EXAMPLE 11

5-(3,5-Di-trifluoromethylphenyl)-2-(2-hydroxy-3-α-cumyl-5-tert-octylphenyl)-2H-benzotriazole The procedure of Example 2 is followed using 5-bromo-2-(2-hydroxy-3-α-cumyl-5-tert-octyl)phenyl)-2H-benzotriazole 1.04 g, 0.002 mol), 3,5-di-trifluoromethylphenylboronic acid (0.54 g, 0.0021 mol), palladium(II) diacetate (0.045 g, 0.0002 mol), triphenylphosphine (0.160 g, 0.0006 mol), 1.2 mL of 2M sodium carbonate (0.25 g, 0.0024 mol), 2 mL of water and 50 mL of isopropanol at 790° C. for five hours. The residue is purified by recrystallization sequentially from isopropanol (20 mL) and acetonitrile (10 mL) to give 0.44 g (34% yield) of the title compound as a light yellow solid melting at 79–81° C.

¹Hnmr (CDCl₃; 499.8494 MHz) δ 0.84 (s, 9H); 1.52 (s, 6H); 1.83 (s, 6H); 1.86 (s, 2H); 7.16–7.32 (overlapping multiplets, 5H); 7.66 (d, 1H); 7.69 (dd, 1H); 7.92 (d, 1H); 8.00 (d, 1H); 8.09 (d, 2H); 8.10 (d, 1H); 8.36 (d, 1H); 11.25 (s, 1H);

¹⁹Fnmr (CDCl₃; 282.3300 MHz) δ −69.4;

Analysis: Calcd for $C_{37}H_{37}F_6N_3O$: C, 67.98; H, 5.71; N, 6.43. Found: C, 67.66; H, 5.66; N, 6.34.

EXAMPLE 12

5-(1,1'-Biphenyl-4-yl)-2-(2-hydroxy-3-α-cumyl-5-tert-octylphenyl)-2H-benzotriazole The procedure of Example 2 is followed using 5-bromo-2-(2-hydroxy-3-α-cumyl-5-tert-octyl)phenyl)-2H-benzotriazole 1.04 g, 0.002 mol), (1,1'-biphenyl-4-yl) boronic acid (0.42 g, 0.0021 mol), palladium(II) diacetate (0.045 g, 0.0002 mol), triphenylphosphine (0.160 g, 0.0006 mol), 1.2 mL of 2M sodium carbonate (0.25 g, 0.0024 mol), 2 mL of water and 50 mL of isopropanol at 79° C. for five hours. The residue is purified by rerystallization sequentially from a mixture of toluene (10 mL) and ethyl acetate (100 mL), and heptane (10 mL) to give 0.46 g (39% yield) of the title compound as an off-white solid melting at 181–183° C.

$^1$Hnmr (CDCl$_3$; 499.8494 MHz) δ 0.84 (s, 9H); 1.53 (s, 6H); 1.83 (s, 6H); 1.86 (s, 2H); 7.13–7.32 (overlapping multiplets, 5H); 7.39 (t, 1H); 7.49 (dd, 2H); 7.63 (d, 1H); 7.67 (d, 2H); 7.75 (m, 4H); 7.76 (dd, 1H); 7.93 (d, 1H); 8.07 (d, 1H); 8.36 (d, 1H); 11.40 (s, 1H);

Analysis: Calcd for C$_{41}$H$_{43}$F$_3$N$_3$O: C, 82.93; H, 7.30; N, 7.08. Found: C, 83.12; H, 7.23; N, 6.88.

EXAMPLE 13

5-(4-Cyanophenyl)-2-(2-hydroxy-3-α-cumyl-5-tert-octylphenyl)-2H-benzotriazole

The procedure of Example 2 is followed using 5-bromo-2-(2-hydroxy-3-α-cumyl-5-tert-octyl)phenyl)-2H-benzotriazole 1.04 g, 0.002 mol), 4-cyanophenylboronic acid (0.42 g, 0.0021 mol), palladium(II) diacetate (0.045 g, 0.0002 mol), triphenylphosphine (0.160 g, 0.0006 mol), 1.2 mL of 2M sodium carbonate (0.25 g, 0.0024 mol), 2 mL of water and 50 mL of isopropanol at 79° C. for five hours. The residue is purified by recrystallization from heptane followed by dry-column chromatography (9:1 heptane:ethyl acetate eluent) to give 0.18 g (17% yield) of the title compound as a light yellow crystalline solid melting at 163–164.5° C.

$^1$Hnmr (CDCl$_3$; 499.8494 MHz) δ 0.84 (s, 9H); 1.52 (s, 6H); 1.83 (s, 6H); 1.86 (s, 2H); 7.15–7.32 (overlapping multiplets, 5H); 7.65 (d, 1H); 7.67 (dd, 1H); 7.76 (d, 2H); 7.79 (d, 2H); 7.97 (d, 1H); 8.05 (d, 1H); 8.35 (d, 1H); 11.30 (s, 1H);

MS (DIP) m/z 542 (M$^+$)

Analysis: Calcd for C$_{36}$H$_{38}$N$_4$O: C, 79.67; H, 7.06; N, 10.32. Found: C, 79.79; H, 7.12; N, 10.19.

EXAMPLE 14

5-Bromo-2-(2-hydroxy-3-α-cumyl-5-tert-octyl)phenyl)-2H-benzotriazole

This compound is an important intermediate for the preparation of the instant compounds by the Suzuki reaction by reaction with various arylboronic acids or esters.

(A) 2-Hydroxy-2'nitro-3-α-cumyl-4'-bromo-5-tert-octylazobenzene

Diazotization and coupling: 96% Sulfuric acid (243 g) is charged to a 2L jacketed reactor and the internal temperature is adjusted to 20° C. 40% (wt/wt) nitrosylsulfuric acid (335.4 g in sulfuric acid, 1.06 mol) is added via an addition funnel keeping the internal temperature below 20° C. At the end of this dilution step, the solution is cooled to 0° C. and 217 g of 92.1% pure 4-bromo-2-nitroaniline (0.921 mol) is added in portions keeping the internal temperature between 15–20° C. The reaction mixture is stirred at room temperature for five hours. Water (674 g) is added over a two-hour period while keeping the internal temperature at 0–5° C. The solution is filtered through a coarse funnel and stored at 0° C. Titration of the diazo solution shows an sulfuric acid assay of 31.8% and a diazo assay of 17.9% (a yield of 86.2% of diazo compound based on the 4-bromo-2-nitroaniline).

In a 1L jacketed reactor is added 94.9 g of 96% pure 2-α-cumyl-4-tert-octylphenol (0.281 mol) and 249.5 g of xylene followed by 4.1 g of HOSTAPUR® SAS 93. The mixture is dissolved at 28° C. and the temperature held there. The diazonium salt solution prepared above (723 g, 0.397 mol) is added to this solution over a period of six hours. At the end of the addition period, the transfer line is rinsed with 10.8 g of water and the reaction mixture is stirred for another 30 minutes. The reaction temperature is raised to 60° C. and stirring stopped. The mixture divided into two phases which are separated. 370.3 g of a xylene solution of 2-hydroxy-2'-nitro-3-α-cumyl-4'-phenyl-5-tert-octylazobenzene is obtained. The xylene is removed under vacuum and methanol is added to crystallize the product.

$^1$Hnmr (CDCl$_3$; 499.8494 MHz) δ 0.83 (s, 9H); 1.44 (s, 6H); 1.78 (s, 2H); 1.79 (s, 6H); 7.13–7.28 (overlapping multiplets, 5H); 7.62 (d, 1H); 7.68 (d, 1H); 7.79 (dd, 1H); 7.85 (d, 1H); 8.19 (d, 1H); 12.94 (s, 1H).

(B) 5-Bromo-2-(2-hydroxy-3-α-cumyl-5-tert-octyl)phenyl)-2H-benzotriazole

To 2-butanol (200 mL) and sodium hydroxide (4.8 g, 0.1203 mol) at 94° C. in a 2L Swiss reaction is added dropwise a solution of 2-hydroxy-2'nitro-3-α-cumyl-4'-phenyl-5-tert-octylazobenzene (24.4 g, 0.043 mol) and 2,3-dichloro-1,4-naphthoquinone (1.14 g, 0.005 mol) in methyl ethyl ketone (60 mL) over a period of 1.5 hours while maintaining the temperature of the reaction mixture over 90° C. Water and methyl ethyl ketone distill off during this period. After the reaction mixture is held for one hour at about 90° C., the reduction is complete as seen by a sample tested by HPLC. The reaction mixture is cooled to 30° C. and 31 mL of 30% sulfuric acid is added all at once. After further cooling to 5° C., the product precipitates along with a mixture of salts. The precipitate is isolated by filtration and freed of salts by repeated washing with water. Organic impurities are removed by washing with 200 mL of cold methanol. The title compound is obtained after drying in a yield of 73% (16.4 g) as a light beige solid melting at 113–117° C.

$^1$Hnmr (CDCl$_3$; 499.8494 MHz) δ 0.83 (s, 9H); 1.51 (s, 6H); 1.81 (s, 6H); 1.85 (s, 2H); 7.15–7.30 (overlapping multiplets, 5H); 7.51 (dd, 1H); 7.64 (d, 1H); 7.75 (d, 1H); 8.04 (d, 1H); 8.31 (d, 1H); 11.15 (s, 1H).

EXAMPLE 15

5-(4-Methoxyphenyl)-2-(2-hydroxy-3-α-cumyl-5-tert-octylphenyl)-2H-benzotriazole

The procedure of Example 2 is followed using 5-bromo-2-(2-hydroxy-3-α-cumyl-5-tert-octyl)phenyl)-2H-benzotriazole 1.56 g, 0.0105 mol), 4-methoxyphenylboronic acid (1.56 g, 0.0105 mol), palladium(II) diacetate (0.090 g, 0.0004 mol), triphenylphosphine (0.315 g, 0.0012 mol), 6 mL of 2M sodium carbonate (1.27 g, 0.0012 mol), 10 mL of water and 250 mL of isopropanol at 90.5° C. for one hour. The residue is purified by dry-column flash chromatography (toluene eluent) and recrystallization from heptane (2X) to give 2.00 g (36.5% yield) of the title compound as light yellow crystals melting at 129–131° C.

$^1$Hnmr (CDCl$_3$; 499.8494 MHz) δ 0.84 (s, 9H); 1.52 (s, 6H); 1.83 (s, 6H); 1.86 (s, 2H); 3.89 (s, 3H); 7.03 (d, 2H); 7.14–7.32 (overlapping multiplets, 5H); 7.61 (d, 2H); 7.62 (d, 1H); 7.68 (dd, 1H); 7.89 (dd, 1H); 7.95 (multiplet, 1H); 8.34 (d, 1H); 11.41 (s, 1H);

Analysis: Calcd for C$_{36}$H$_{41}$N$_3$O$_2$: C, 78.94; H, 7.54; N, 7.67. Found: C, 79.11; H, 7.43; N, 7.59.

EXAMPLE 16

1,4-Bis[2-(2-hydroxy-3-α-cumyl-5-tert-octylphenyl)-2H-benzotriazol-5-yl]benzene

The procedure of Example 2 is followed using 5-bromo-2-(2-hydroxy-3-α-cumyl-5-tert-octyl)phenyl)-2H- benzotriazole (5.73 g, 0.011 mol), 1,4-phenylenebis(boronic acid) (0.83 g, 0.005 mol), palladium(II) diacetate (0.090 g, 0.0004 mol), triphenylphosphine (0.315 g, 0.0012 mol), 6 mL of 2M sodium carbonate (1.27 g, 0.012 mol), 10 mL of water and 250 mL of isopropanol at 88° C. for three hours. The residue is purified by dry-column flash chromatography (toluene eluent) and recrystallization from heptane to give 2.58 g (53.9% yield) of the title compound as light yellow crystals melting at 247–249° C.

(Dry-column flash chromatography is described by J. Leonard, B. Lygo and G. Proctor, in "Advanced Practical Organic Chemistry", 2nd Edition, Blackie Academic & Professional, London, 1965, pp 215–216.)

$^1$Hnmr (CDCl$_3$; 499.8494 MHz) δ 0.84 (s, 18H); 1.53 (s, 12H); 1.84 (s, 12H); 1.87 (s, 4H); 7.15–7.34 (overlapping multiplets, 10H); 7.64 (d, 2H); 7.77 (dd, 2H); 7.80 (s, 4H); 7.95 (d, 2H); 8.09 (d, 2H); 8.36 (d, 2H); 11.40 (s, 2H).

Analysis: Calcd for $C_{64}H_{72}N_6O_2$: C, 80.30; H, 7.58; N, 8.78. Found: C, 80.20; H, 7.63; N, 8.59.

EXAMPLE 17

5-(4-Methoxyphenyl)-2-(2-hydroxy-3,5-di-tert-butylphenyl)-2H-benzotriazole

The procedure of Example 2 is followed using 5-chloro-2-(2-hydroxy-3-α-cumyl-5-tert-octyl)phenyl)-2H-benzotriazole 3.58 g, 0.01 mol), 4-methoxyphenylboronic acid (3.04 g, 0.002 ml), palladium(II) diacetate (0.224 g, 0.001 mol), 2-(dicyclohexylphosphino)biphenyl (0.701 g, 0.002 mol), potassium fluoride (1.16 g, 0.02 mol) and 200 mL of dioxane at 88° C. for two hours. The residue is purified by dry-column flash chromatography (silica gel, 93:5 heptane:ethyl acetate eluent) followed by dissolving in 50 mL of toluene and extraction with 5% aqueous sodium bicarbonate (20 mL) and saturated sodium chloride solution (20 mL). The toluene solution is dried over anhydrous sodium sulfate and the solvent removed under vacuum to give 0.60 g (14% yield) of the title compound as light yellow solid.

$^1$Hnmr (CDCl$_3$; 499.8494 MHz) δ 1.42 (s, 9H); 1.53 (s, 9H); 3.90 (s, 3H); 7.05 (d, 2H); 7.44 (d, 1H); 7.64 (d, 2H); 7.73 (dd, 1H); 7.98 (d, 1H); 8.04 (d, 1H); 8.31 (d, 1H); 11.79 (s, 1H).

MS (DIP) 429 (M$^+$).

EXAMPLE 18

5-(4-Trifluoromethylphenyl)-2-(2-hydroxy-3,5-di-tert-butylphenyl)-2H-benzotriazole The procedure of Example 2 is followed using 5-chloro-2-(2-hydroxy-3-α-cumyl-5-tert-octyl)phenyl)-2H-benzotriazole 3.58 g, 0.01 mol), 4-trifluoromethylphenylboronic acid (2.85 g, 0.015 ml), palladium(II) diacetate (0.224 g, 0.001 mol), 2-(di-tert-butylphosphino)biphenyl (0.596 g, 0.002 mol), potassium fluoride (1.16 g, 0.02 mol) and 200 mL of dioxane at 88° C. for two hours. The residue is purified by dry-column flash chromatography (silica gel, 93:5 heptane:ethyl acetate eluent) to give 0.64 g (13.7% yield) of the title compound as light yellow solid.

MS (DIP) 467 (M$^+$).

Analysis: Calcd for $C_{36}H_{41}N_3O_2$: C, 78.94; H, 7.54; N, 7.67. Found: C, 79.11; H, 7.43; N, 759.

EXAMPLE 19

Polycarbonate

The durability of representative instant benzotriazoles in thermoplastic substrates is determined by incorporating various test compounds into solvent cast films of polycarbonate resins. The free standing films are mounted into cardboard holders, secured in metal frames and exposed in an Atlas C165 Xenon-arc Weather-Ometer under dry conditions according to ASTM G26. Loss of UV absorber is determined by monitoring the loss of diagnostic UV absorption.

Polycarbonate flake (LEXAN® 145, General Electric) is dissolved in methylene chloride at room temperature along with between 1 and 3% by weight of test benzotriazole, based on the polycarbonate. Films are cast using a calibrated drawdown bar to prepare 1 mil thick film after drying.

The instant compounds are particularly efficacious when used in thermoplastic compositions, such as polycarbonate. This is shown by the reduction in absorbance loss after exposure to actinic radiation.

EXAMPLE 20

Polycarbonate

Polycarbonate films of about 1 mil thickness and containing a UV absorber are prepared by dissolving polycarbonate granules (LEXAN® 145, General Electric) and UV absorbers in methylene chloride and casting the films on a glass plate using a drawdown bar. The films are exposed for 750 hours in a Xenon Arc Weather-Ometer according to ASTM G26 test method and the color change (ΔYI) versus that for unexposed films are recorded below. The color measurements (yellowness index—YI) are carried out on an ACS spectrophotometer, small area view, spectral component included d/8, D65, 10° observer, YI 1925 for unexposed and exposed samples after 750 hours.

The instant compounds are particularly efficacious when used in thermoplastic compositions, such as polycarbonate. This is shown by the reduction of yellowing (ΔYI) after exposure to actinic radiation.

EXAMPLE 21

Poly(methyl methacrylate)

The durability of representative instant benzotriazoles in thermoplastic substrates is determined by incorporating various test compounds into solvent cast films of a poly(methyl methacrylate) (PMMA) resin. The free standing films are mounted into cardboard holders, secured in metal frames and exposed in an Atlas C165 Xenon-arc Weather-Ometer under dry conditions according to ASTM G26. Loss of UV absorber is determined by monitoring the loss of diagnostic UV absorption as described earlier. Performance is measured by a change in color or the physical integrity of the film, or in loss of absorbance of the UV absorber at λmax.

Poly(methyl methacrylate), medium molecular weight, Aldrich, is dissolved in methylene chloride at room temperature along with between 1 and 3% by weight of test benzotriazole, based on the PMMA resin. Films are cast using a calibrated drawdown bar to prepare 1 mil thick film after drying.

The instant compounds are particularly efficacious when used in thermoplastic compositions, such as poly(methyl methacrylate). This is shown by the reduction in absorbance loss after exposure to actinic radiation.

EXAMPLE 22

Incorporation into Photographic Layers

A gelatin coat of the following composition (per m$^2$) is applied in the customary manner to a polyester base.

| Components | Amount |
|---|---|
| Gelatin | 1200 mg |
| Tricresyl Phosphate | 510 mg |
| Hardener* | 40 mg |
| Wetting Agent** | 100 mg |
| Test UV Absorber | 400 mg |

*potassium salt of 2-hydroxy-4,6-dichloro-s-triazine
**sodium 4,8-diisobutylnaphthalene-2-sulfonate The gelatin coats are dried at 20° C. for seven days.

When the instant UV absorbers are used, clear transparent coats are obtained which are suitable for photographic recording material for example as a UV filter coat. This is seen by measuring the % Change in Initial Optical Density (2.0) after UV exposure. The instant compounds when used in a photographic layer are extremely photostable.

EXAMPLE 23

Automotive Coating Compositions

To ascertain the effect on thermal durability and loss rate from a high solids thermoset acrylic coating containing an instant benzotriazole UV absorber, the following tests are carried out.

A high solids thermoset acrylic clear coat is prepared by mixing an experimental acrylic polyol resin and hexamethoxymethylmelamine (Resimene® 747, Monsanto) at a solids ratio of 60/40. The dodecylbenzene sulfonic acid catalyst (Nacure® 5225; King Industries) is added at 0.70% by weight. A flow aid Modaflow® (Monsanto) is added at 0.25% by weight to form a model acrylic melamine resin system.

The model clear coat is reduced with xylene to a viscosity of 26–27 second using a Zahn #2 cup and applied via a conventional air spray at 50 psi (3.5 Kg/cm$^2$) over a 1"×3" (2.54 cm×7.62 cm) quartz slide. Cure is achieved by baking the slide for 30 minutes at 260° F. (127° C.). The clear coat is stabilized with 1% by weight of a hindered amine light stabilizer, bis-(1-octyloxy-2,2,6,6-tetramethylpiperidin-4-yl)sebacate, (TINUVIN® 123, Ciba). The various test benzotriazole UV absorbers are incorporated at the 5 mmol % by weight in the clear coat. The film thickness on the quartz slides range from 1. 15 to 1.41 mils (0.029 to 0.036 mm).

The films on the quartz slides are weathered according to the following conditions in Xenon Arc Weather-Ometer with a controlled irradiance at 6500 W, using inner quartz and outer borosilicate S-type filter. The irradiation cycle is as follows: 40 minutes of straight irradiation with no water spray, followed by 20 minutes of light plus front spray, followed by 60 minutes of light irradiation and finally by 60 minutes dart plus rear spray (condensation). The setting is at 0.55 W/M$^2$ at 340 nm, 1.98 kJ/hour. In the light cycle the black panel temperature is controlled at 70±2° C. The relative humidity in the light cycle is in the range of 50–55% and in the dark cycle 100%. The absorbance of the long wavelength UV band as a function of Xenon arc weathering hours are recorded.

To follow the loss of UV absorbers from the clear coats, UV spectra are measured initially and after weathering at regular time intervals. The UV spectrophotometer measures absorbance linearly up to 5.5 absorbance units using a reference beam attenuation technique.

It is assumed that the degradation products from the UV absorber do not contribute to the UV spectrum. This is tested by following the ratio of absorbance of the band at about 300 nm and the band at about 340 nm. The ratio does not change upon weathering the sample. This suggests that the UV spectrum of the weathered films correspond to the amount of UV absorber remaining in the film with very little if any contribution to the spectrum by photo degradants.

Representative benzotriazole test compounds are incorporated into a high solid thermoset acrylic melamine resin at a concentration of 3% by weight to give equal molar concentrations of the test benzotriazole in equal film thickness and sufficient to give a starting absorbance of approximately 2.0 absorbance units.

The instant benzotriazoles are especially durable in automotive coatings as judged by low loss rates.

EXAMPLE 24

Color Change of a White Unscented Candle Wax Under Fluorescent Lamp Exposure A variety of different stabilizers are evaluated in a white unscented candle wax under fluorescent lamp exposure. The stabilizers include a compound of Example 2 alone or with a hindered amine like bis(1,2,2,6,6-pentamethylpiperidin-4-yl)sebacate, TINUVIN® 292, CIBA or bis(1-octyloxy-2,2,6,6-tetramethylpiperidin-4-yl)sebacate, TINUVIN® 123, CIBA. The ΔE values represent the change in color after exposure. A low ΔE value indicates less change in color and is highly desired.

The instant compound alone or with the hindered amine provides excellent protection to the white unscented candle wax from discoloration.

EXAMPLE 25

Color Fade of Green Scented Candle Wax Under UV Lamp Exposure

A variety of different stabilizers are evaluated in green scented candle wax obtained from the Candle Corporation of America under UV lamp exposure at 368 nm wavelength. The stabilizers include a compound of Example 1 alone or with a hindered amine like bis(1,2,2,6,6-pentamethylpiperidin-4-yl)sebacate, TINUVIN® 292, CIBA or bis(1-tyloxy-2,2,6,6-tetramethylpiperidin-4-yl)sebacate, TINUVIN® 123, CIBA. The ΔE values represent the change in color after exposure. A low ΔE value indicates less change in color and is highly desired.

The instant compound alone or with the hindered amine provides excellent protection to the green scented candle wax from dye fade.

EXAMPLE 26

Color Fade of a Blue Unscented Candle Wax Under UV Lamp Exposure

A variety of different stabilizers are evaluated in blue unscented candle wax under UV lamp exposure at 368 nm wavelength. The stabilizers include a compound of Example 1 alone or with a hindered amine like bis(1,2,2,6- pentamethylpiperidin-4-yl)sebacate, TINUVIN® 292, CIBA or bis(1-octyloxy-2,2,6,6-tetramethylpiperidin-4-yl) sebacate, TINUVIN® 123, CIBA. The ΔE values represent the change in color after exposure. A low ΔE value indicates less change in color and is highly desired.

The instant compound alone or with the hindered amine provides excellent protection to the blue unscented candle wax from dye fade.

EXAMPLE 27

Color Fade of Pink Scented Candle Wax Under Fluorescent Lamp Exposure

Different stabilizers are evaluated in pink scented candle wax obtained from the Candle-Lite Corporation under fluorescent lamp exposure. The ΔE values represent the change in color after the indicated days of exposure. A low ΔE value indicates less change in color and is highly desired.

| | ΔE after | | |
|---|---|---|---|
| Sample* (wt % add) | 8.9 days | 11.8 days | 22.3 days |
| Blank (no add) | 8.10 | 10.22 | 12.12 |
| A (0.3%) | 8.72 | 10.48 | 12.91 |
| F (0.3%) | 6.75 | 6.50 | 8.58 |
| C (0.15%) + D (0.15%) | 2.07 | 4.37 | 5.94 |
| A (0.15%) + B (0.15%) | 3.18 | 2.20 | 2.79 |
| E (0.15%) + B (0.15%) | 4.21 | 3.24 | 2.13 |
| F (0.15%) + G (0.15%) | 1.77 | 2.49 | 4.16 |

*A is bis(1-octyloxy-2,2,6,6-tetramethylpiperidin-4-yl) sebacate, TINUVIN ® 123, CIBA).
B is 5-(4-trifluoromethylphenyl)-2-(2-hydroxy-3-α-cumyl-5-tert-octylphenyl)-2H-benzo-triazole, Compound of Example 2.
C is 2-(2-hydroxy-5-tert-octylphenyl)-2H-benzotriazole, TINUVIN ® 329, CIBA.
D is 4-octyloxy-2-hydroxybenzophenone, CHIMASSORB ® 81, CIBA.
E is 1,3,5-tris[N-cyclohexyl-N-(2,2,6,6-tetramethylpiperazin-3-on-4-yl)amino]-s-triazine, GOODRITE ® 3150, Goodrich.
F is bis(1,2,2,6,6-pentamethylpiperidin-4-yl) sebacate, TINUVIN ® 292, CIBA.
G is 1,4-bis[2-(2-hydroxy-3-α-cumyl-5-tert-octylphenyl)-2H-benzotriazol-5-yl]benzene, Compound of Example 16.

These data show that a hindered amine in combination with an instant UV absorber protects the pink scented candle wax far better than the hindered amine or a UV absorber alone.

EXAMPLE 28

Color Fade of Pink Scented Candle Wax Under UV Lamp Exposure

A variety of different stabilizers are evaluated in pink scented candle wax obtained from the Candle-Lite Corporation under UV lamp exposure. The ΔE values represent the change in color after the indicated days of exposure. A low ΔE value indicates less change in color and is highly desired.

| | ΔE after | | |
|---|---|---|---|
| Sample* (wt % add) | 7.6 days | 13.5 days | 36.7 days |
| Blank (no add) | 16.16 | 16.44 | 20.27 |
| A (0.3%) | 13.93 | 15.20 | 15.88 |
| F (0.3%) | 14.79 | 16.41 | 17.53 |
| C (0.15%) + D (0.15%) | 8.93 | 7.72 | 9.62 |
| F (0.15%) + G (0.15%) | 2.99 | 3.72 | 5.59 |
| A (0.15%) + B (0.15%) | 1.54 | 1.67 | 3.08 |
| E (0.15%) + B (0.15%) | 3.19 | 2.76 | 2.10 |

*A is bis(1-octyloxy-2,2,6,6-tetramethylpiperidin-4-yl) sebacate, TINUVIN ® 123, CIBA).
B is 5-(4-trifluoromethylphenyl)-2-(2-hydroxy-3-α-cumyl-5-tert-octylphenyl)-2H-benzo-triazole, Compound of Example 2.
C is 2-(2-hydroxy-5-tert-octylphenyl)-2H-benzotriazole, TINUVIN ® 329, CIBA.
D is 4-octyloxy-2-hydroxybenzophenone, CHIMASSORB ® 81, CIBA.
E is 1,3,5-tris[N-cyclohexyl-N-(2,2,6,6-tetramethylpiperazin-3-on-4-yl)amino]-s-triazine, GOODRITE ® 3150, Goodrich.
F is bis(1,2,2,6,6-pentamethylpiperidin-4-yl) sebacate, TINUVIN ® 292, CIBA.
G is 1,4-bis[2-(2-hydroxy-3-α-cumyl-5-tert-octylphenyl)-2H-benzotriazol-5-yl]benzene, Compound of Example 16.

These data show that a hindered amine in combination with an instant UV absorber protects the pink scented candle wax far better than conventional UV absorbers or a hindered amine alone.

EXAMPLE 29

Color Fade of Gray Scented Candle Wax Under Fluorescent Lamp Exposure

A variety of different stabilizers are evaluated in gray scented candle wax obtained from the Candle-Lite Corporation under fluorescent lamp exposure. The ΔE values represent the change in color after the indicated days of exposure. A low ΔE value indicates less change in color and is highly desired.

| | ΔE after | | |
|---|---|---|---|
| Sample* (wt % add) | 4.9 days | 10.9 days | 33.9 days |
| Blank (no add) | 9.66 | 11.97 | 16.01 |
| A (0.3%) | 9.67 | 10.89 | 11.32 |
| F (0.3%) | 4.88 | 6.16 | 7.55 |
| C (0.15%) + D (0.15%) | 1.56 | 4.33 | 8.52 |
| A (0.15%) + B (0.15%) | 1.74 | 2.01 | 4.50 |
| A (0.15%) + G (0.15%) | 0.80 | 1.99 | 4.09 |
| F (0.15%) + B (0.15%) | 1.21 | 1.24 | 3.42 |

*A is bis(1-octyloxy-2,2,6,6-tetramethylpiperidin-4-yl) sebacate, TINUVIN ® 123, CIBA).
B is 5-(4-trifluoromethylphenyl)-2-(2-hydroxy-3-α-cumyl-5-tert-octylphenyl)-2H-benzo-triazole, Compound of Example 2.
C is 2-(2-hydroxy-5-tert-octylphenyl)-2H-benzotriazole, TINUVIN ® 329, CIBA.
D is 4-octyloxy-2-hydroxybenzophenone, CHIMASSORB ® 81, CIBA.
F is bis(1,2,2,6,6-pentamethylpiperidin-4-yl) sebacate, TINUVIN ® 292, CIBA.
G is 1,4-bis[2-(2-hydroxy-3-α-cumyl-5-tert-octylphenyl)-2H-benzotriazol-5-yl]benzene, Compound of Example 16.

These data show that a hindered amine in combination with an instant UV absorber protects the gray scented candle wax far better than conventional UV absorbers or a hindered amine alone.

EXAMPLE 30

Color Fade of Gray Scented Candle Wax Under UV Lamp Exposure

A variety of different stabilizers are evaluated in gray scented candle wax obtained from the Candle-Lite Corporation under UV lamp exposure. The ΔE values represent the change in color after the indicated days of exposure. A low ΔE value indicates less change in color and is highly desired.

| Sample* (wt % add) | ΔE after | | |
|---|---|---|---|
| | 2.8 days | 8.9 days | 22.6 days |
| Blank (no add) | 22.20 | 28.98 | 30.07 |
| A (0.3%) | 20.83 | 27.37 | 25.37 |
| F (0.3%) | 23.88 | 26.40 | 25.38 |
| C (0.15%) + D (0.15%) | 2.30 | 7.06 | 10.96 |
| F (0.15%) + G (0.15%) | 1.98 | 3.68 | 4.89 |
| A (0.15%) + B (0.15%) | 1.10 | 2.58 | 4.14 |
| F (0.15%) + B (0.15%) | 1.01 | 2.18 | 3.58 |

*A is bis(1-octyloxy-2,2,6,6-tetramethylpiperidin-4-yl) sebacate, TINUVIN ® 123, CIBA).
B is 5-(4-trifluoromethylphenyl)-2-(2-hydroxy-3-α-cumyl-5-tert-octylphenyl)-2H-benzo-triazole, Compound of Example 2.
C is 2-(2-hydroxy-5-tert-octylphenyl)-2H-benzotriazole, TINUVIN ® 329, CIBA.
D is 4-octyloxy-2-hydroxybenzophenone, CHIMASSORB ® 81, CIBA.
F is bis(1,2,2,6,6-pentamethylpiperidin-4-yl) sebacate, TINUVIN ® 292, CIBA.
G is 1,4-bis[2-(2-hydroxy-3-α-cumyl-5-tert-octylphenyl)-2H-benzotriazol-5-yl]benzene, Compound of Example 16.

These data show that a hindered amine in combination with an instant UV absorber protects the gray scented candle wax far better than conventional UV absorbers or a hindered amine alone.

EXAMPLE 31

Color Fade of White Scented Candle Wax Under Fluorescent Lamp Exposure

A variety of different stabilizers are evaluated in white scented candle wax obtained from the Candle-Lite Corporation under fluorescent lamp exposure. The ΔE values represent the change in color after the indicated days of exposure. A low ΔE value indicates less change in color and is highly desired.

| Sample* (wt % add) | ΔE after | | |
|---|---|---|---|
| | 4.0 days | 14.7 days | 33.0 days |
| Blank (no add) | 27.56 | 33.74 | 34.68 |
| A (0.3%) | 13.31 | 22.24 | 26.35 |
| F (0.3%) | 21.46 | 30.91 | 32.06 |
| C (0.15%) + D (0.15%) | 9.39 | 17.68 | 21.24 |
| F (0.15%) + G (0.15%) | 12.47 | 20.93 | 20.14 |
| A (0.15%) + B (0.15%) | 2.87 | 6.27 | 9.32 |
| E (0.15%) + B (0.15%) | 6.05 | 14.00 | 18.32 |

*A is bis(1-octyloxy-2,2,6,6-tetramethylpiperidin-4-yl) sebacate, TINUVIN ® 123, CIBA).
B is 5-(4-trifluoromethylphenyl)-2-(2-hydroxy-3-α-cumyl-5-tert-octylphenyl)-2H-benzo-triazole, Compound of Example 2.
C is 2-(2-hydroxy-5-tert-octylphenyl)-2H-benzotriazole, TINUVIN ® 329, CIBA.
D is 4-octyloxy-2-hydroxybenzophenone, CHIMASSORB ® 81, CIBA.
E is 1,3,5-tris[N-cyclohexyl-N-(2,2,6,6-tetramethylpiperazin-3-on-4-yl)amino]-s-triazine, GOODRITE ® 3150, Goodrich.
F is bis(1,2,2,6,6-pentamethylpiperidin-4-yl) sebacate, TINUVIN ® 292, CIBA.
G is 1,4-bis[2-(2-hydroxy-3-α-cumyl-5-tert-octylphenyl)-2H-benzotriazol-5-yl]benzene, Compound of Example 16.

These data show that a hindered amine in combination with an instant UV absorber protects the white scented candle wax far better than conventional UV absorbers or a hindered amine alone.

EXAMPLE 32

Color Fade of White Scented Candle Wax Under UV Lamp Exposure

A variety of different stabilizers are evaluated in white scented candle wax obtained from the Candle-Lite Corporation under UV lamp exposure. The ΔE values represent the change in color after the indicated days of exposure. A low ΔE value indicates less change in color and is highly desired.

| Sample* (wt % add) | ΔE after | | |
|---|---|---|---|
| | 5.9 days | 16.6 days | 35.0 days |
| Blank (no add) | 42.90 | 45.57 | 45.14 |
| A (0.3%) | 34.65 | 36.64 | 35.07 |
| F (0.3%) | 35.55 | 33.80 | 29.30 |
| C (0.15%) + D (0.15%) | 24.48 | 28.86 | 27.80 |
| F (0.15%) + G (0.15%) | 14.53 | 21.47 | 22.17 |
| A (0.15%) + B (0.15%) | 7.71 | 10.57 | 12.97 |
| E (0.15%) + B (0.15%) | 9.01 | 14.03 | 15.50 |

*A is bis(1-octyloxy-2,2,6,6-tetramethylpiperidin-4-yl) sebacate, TINUVIN ® 123, CIBA).
B is 5-(4-trifluoromethylphenyl)-2-(2-hydroxy-3-α-cumyl-5-tert-octylphenyl)-2H-benzo-triazole, Compound of Example 2.
C is 2-(2-hydroxy-5-tert-octylphenyl)-2H-benzotriazole, TINUVIN ® 329, CIBA.
D is 4-octyloxy-2-hydroxybenzophenone, CHIMASSORB ® 81, CIBA.
E is 1,3,5-tris[N-cyclohexyl-N-(2,2,6,6-tetramethylpiperazin-3-on-4-yl)amino]-s-triazine, GOODRITE ® 3150, Goodrich.
F is bis(1,2,2,6,6-pentamethylpiperidin-4-yl) sebacate, TINUVIN ® 292, CIBA.
G is 1,4-bis[2-(2-hydroxy-3-α-cumyl-5-tert-octylphenyl)-2H-benzotriazol-5-yl]benzene, Compound of Example 16.

These data show that a hindered amine in combination with an instant UV absorber protects the white scented candle wax far better than conventional UV absorbers or a hindered amine alone.

EXAMPLE 33

Spectral Properties of Substituted 5-Arylbenzotriazole UV Absorbers of Formulas I and II

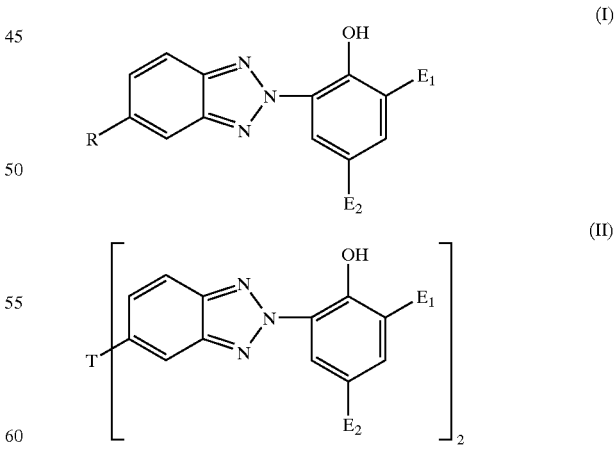

The following table shows the absorption maxima and molar extinction coefficients of a number of 2H-benzotriazole UV absorbers of formulas I and II where $E_1$ is α-cumyl and $E_2$ is tert-octyl unless otherwise indicated. A state-of-the-art commercial benzotriazole UV absorber, 2-[2-hydroxy-3,5-di-(α,α-dimethylbenzyl)phenyl]-2H-benzotriazole (TINUVIN® 900, CIBA) and a number of instant 5-aryl substituted compounds are tested. The concentrations of each of the samples are identical, namely 20 mg/L in ethyl acetate. The absorption λ maxima of the instant compounds at 350 to 369 nm are red-shifted, i.e. shifted towards the visible relative to the commercial control, which has an absorption λ maximum at 342 nm (∈15,500). The molar extinction coefficients ∈ of the 5-aryl substituted compounds substituted instant compounds far exceed that of the control compound at the absorption λ maxima.

Absorption Maxima and Molar Extinction Coefficients of Benzotriazole UV Absorbers

| Compound of | nm | Molar ∈ | R or T 5-Substitution | Hammett Constant |
|---|---|---|---|---|
| Control* | 342 | (15,500) | hydrogen | $\sigma_p = 0.0$ |
| Example 7 | 355 | (17,745) | 3-trifluorophenyl | $\sigma_m = +0.46$ |
| Example 11 | 357 | (19,727) | 3,5-bis-CF$_3$phenyl | $\sigma_m = +0.46$ |
| Example 8 | 350 | (21,035) | 2-trifluorophenyl | |
| Example 15 | 362 | (21,506) | 5-methoxyphenyl | $\sigma_p = -0.27$ |
| Example 2 | 356 | (23,910) | 4-trifluorophenyl | $\sigma_p = +0.53$ |
| Example 13 | 358 | (23,981) | 4-cyanophenyl | $\sigma_p = +0.70$ |
| Example 10 | 356 | (25,690) | phenyl | $\sigma_p = 0.0$ |
| Example 12 | 361 | (31,903) | 1,1'-biphenyl-4-yl | $\sigma_p = +0.05$ |
| Example 16** | 369 | (52,629) | p-phenylenebis | |
| Example 17*** | 360 | (25,453) | 5-methoxyphenyl | $\sigma_p = -0.27$ |

*Control is 2-[2-hydroxy-3,5-di-(α,α-dimethlbenzyl)phenyl]-2H-benzotriazole, TINUVIN ® 900, CIBA.
**Example 16 is a compound of formula II where T is p-phenylene, $E_1$ is α-cumyl and $E_2$ is tert-octyl.
***Example 17 is a compound of formula I where $E_1$ and $E_2$ are each tert-butyl.

What is claimed is:

1. A process for the preparation of a compound of formula I

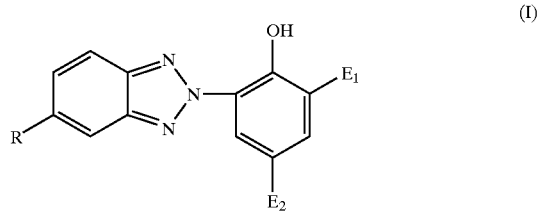

(I)

by the reaction of an arylboronic acid or ester of formula III

(III)

where $R_1$ and $R_2$ are independently hydrogen, alkyl of 1 to 12 carbon atoms, or $R_1$ and $R_2$ together are alkylene of 2 to 4 carbon atoms;

with a 5-substituted benzotriazole of formula V

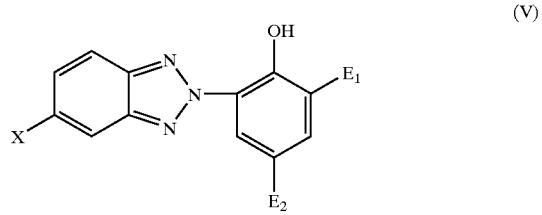

(V)

where X is chloro, bromo or iodo, or tosylate, in the presence of an effective amount of a palladium(II) catalyst at a temperature between 10 to 100° C., and where R is phenyl, naphthyl, biphenylyl, 9-phenanthryl or said phenyl, naphthyl, biphenylyl or 9-phenanthryl substituted by one to three alkyl of 1 to 18 carbon atoms, phenylalkyl of 7 to 15 carbon atoms, $R_3S$—, $R_3SO$—, $R_3SO_2$, aryl of 6 to 10 carbon atoms, perfluoroalkyl of 1 to 12 carbon atoms, halogen, nitro, cyano, carboxyl, alkoxycarbonyl of 2 to 19 carbon atoms, hydroxyl, alkoxy of 1 to 18 carbon atoms, aryloxy of 6 to 10 carbon atoms, aralkoxy of 7 to 15 carbon atoms, vinyl, acetyl, acetamido, amino, dialkylamino of 2 to 12 carbon atoms, formyl, thioalkoxy of 1 to 18 carbon atoms, hydroxymethyl, aminomethyl, halomethyl, sulfato, phosphato or where any two substituents form a benzo ring with the aryl moiety to which they are attached, $R_3$ is alkyl of 1 to 18 carbon atoms, phenylalkyl of 7 to 15 carbon atoms or aryl of 6 to 10 carbon atoms, $E_1$ is hydrogen, straight or branched alkyl of 1 to 24 carbon atoms, phenylalkyl of 7 to 15 carbon atoms, phenyl, or said phenyl or said phenylalkyl substituted on the phenyl ring by 1 to 4 alkyl of 1 to 4 carbon atoms, $E_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; or $E_2$ is alkyl of 1 to 24 carbon atoms or alkenyl of 2 to 18 carbon atoms substituted by one or more —OH, —OCOE$_3$, —NH$_2$, —NHCOE$_3$ or —COOE$_3$, or mixtures thereof; or said alkyl or said alkenyl interrupted by one or more —O— which can be unsubstituted or substituted by one or more —OH groups; where $E_3$ is hydrogen or alkyl of 1 to 24 carbon atoms, and where said alkyl is interrupted by one or more —O— and which can be substituted by one or more —OH or —OR$_{21}$ groups where $R_{21}$ is alkyl of 1 to 12 carbon atoms; and with the proviso that when $E_1$ is hydrogen or alkyl, R is not phenyl.

2. A process according to claim 1 wherein X is bromo.
3. A process according to claim 1 wherein the reaction is carried out at a temperature between 50 to 95° C.
4. A process according to claim 1 wherein the amount of palladium(II) catalyst is 0.01 to 10 mol percent.
5. A process according to claim 1 wherein additionally a ligand is present.
6. A process according to claim 5 wherein the ligand is triphenylphosphine, 2-(di-tert-butylphosphino)biphenyl, 1,1'-bis[2,4,8, 1 0-tetrakis(tert-butyl)-dibenzo[d,f][1,3,2] dioxaphosphepin-6-yl]-ferrocene, tris(2,4-di-tert-butylphenyl)phosphite or 2,2',2"-nitrilo[triethyl-tris(3,3',5, 5'-tetra-tert-butyl-1,1'-biphenyl-2,2'-diyl)phosphite].
7. A process according to claim 6 wherein the ligand is triphenylphosphine.
8. A process according to claim 1 wherein the process is an anhydrous process with dioxane as solvent and potassium fluoride as a base.
9. A process according to claim 1 wherein the process is carried out using n-propanol or isopropanol as solvent with a small amount of water present and aqueous sodium carbonate as base.

* * * * *